United States Patent [19]
Giusti et al.

[11] Patent Number: 5,644,049
[45] Date of Patent: Jul. 1, 1997

[54] BIOMATERIAL COMPRISING HYALURONIC ACID AND DERIVATIVES THEREOF IN INTERPENETRATING POLYMER NETWORKS (IPN)

[75] Inventors: Paolo Giusti, Pisa; Lanfranco Callegaro, Padua, both of Italy

[73] Assignee: M.U.R.S.T. Italian Ministry for Universitites and Scientific and Technology Research, Rome, Italy

[21] Appl. No.: 367,137

[22] PCT Filed: Jul. 5, 1993

[86] PCT No.: PCT/EP93/01727

§ 371 Date: Feb. 23, 1995

§ 102(e) Date: Feb. 23, 1995

[87] PCT Pub. No.: WO94/01468

PCT Pub. Date: Jan. 20, 1994

[30] Foreign Application Priority Data

Jul. 3, 1992 [IT] Italy .................... PD92A0121

[51] Int. Cl.⁶ .................... C08B 37/08; A61K 31/715
[52] U.S. Cl. .................... 536/53; 536/18.7; 536/55; 536/55.1; 536/55.2; 523/113; 523/114; 523/115
[58] Field of Search .................... 536/18.7, 53, 55, 536/55.1, 55.2; 514/54, 62; 523/113, 114, 115

[56] References Cited

U.S. PATENT DOCUMENTS

| | | | |
|---|---|---|---|
| 4,582,865 | 4/1986 | Balazs et al. | 524/29 |
| 4,678,468 | 7/1987 | Hiroyoshi | 623/1 |
| 4,713,448 | 12/1987 | Balazs et al. | 536/55.1 |
| 4,731,078 | 3/1988 | Stoy et al. | 623/6 |
| 4,747,953 | 5/1988 | Zupancic et al. | 210/651 |
| 4,762,168 | 8/1988 | Kawabe et al. | 165/11.1 |
| 4,851,521 | 7/1989 | della Valle et al. | 536/55.1 |
| 4,965,353 | 10/1990 | della Valle et al. | 536/55.1 |
| 5,191,016 | 3/1993 | Yalpani | 525/54.2 |
| 5,409,904 | 4/1995 | Hecht et al. | 514/23 |
| 5,410,016 | 4/1995 | Hubbell et al. | 528/354 |

FOREIGN PATENT DOCUMENTS

| | | |
|---|---|---|
| 0138572 | 4/1985 | European Pat. Off. . |
| 0459378 | 12/1991 | European Pat. Off. . |
| 0466300 | 1/1992 | European Pat. Off. . |
| 93/11803 | 6/1993 | WIPO . |

OTHER PUBLICATIONS

Wang et al. Chin. Chem. Lett. 1991, 2(12), 971–972.
Weigel et al., J. Theor. Biol. 119, 219–234 (1986).
Sperling, CHEMTECH, pp. 104–109 (1988).
Hastings et al., Macromolecular Biomaterials, CRC Press (1984), Table of Contents Only.
Bruck, Properties of Biomaterials in the Physiological Environment, CRC Press (1980), Table of Contents Only.
British Pharmacopea, p. 127 (1980).
Salovey et al., The Bell System Techn. Journal, p. 1397 (1961).
Okada, J. Applied Polymer Science, 7, pp. 695–701, 703–708 & 1153–1163 (1963).
Tatara, J. Polymer Sci., Symposium No. 54, p. 283 (1976).

Primary Examiner—Gary L. Kunz
Assistant Examiner—Kathleen Kahler Fonda
Attorney, Agent, or Firm—Birch, Stewart, Kolasch & Birch, LLP

[57] ABSTRACT

Provided is a biomaterial comprising an interpenetrating polymer network (IPN), wherein one of the polymer components is an acidic polysaccharide or a semi-synthetic derivative thereof. The polysaccharide can be hyaluronic acid, and the second polymer component can be a non-toxic, non-carcinogenic synthetic chemical polymer. The derivative can be a total or partial hyaluronic acid ester or a hyaluronic acid salt. The ester or salt can be formed with a pharmacologically active molecule. Methods for preparing the IPN are also disclosed. The acidic polysaccharide or derivative thereof and the synthetic chemical polymer comprising the IPN can be cross-linked, or the synthetic chemical polymer can be grafted onto the acidic polysaccharide. The cross-linking or grafting can be achieved using compounds capable of generating radicals, or via functional groups on the acidic polysaccharide and the synthetic chemical polymer. The IPN can be formed prior to cross-linking or grafting. The IPN biomaterial can be in the form of a film, a membrane, a sponge, a hydrogel, a guide channel, a thread, a gauze, or a non-woven tissue. Such IPN biomaterials can be used in the biomedical and sanitary fields, including dermatology, urology, orthopedics, otologic microsurgery, otoneurology, functional, post-traumatic and rhinosinusal endoscopic microsurgery, plastic surgery, and in the cardiovascular system.

19 Claims, No Drawings

BIOMATERIAL COMPRISING HYALURONIC ACID AND DERIVATIVES THEREOF IN INTERPENETRATING POLYMER NETWORKS (IPN)

BACKGROUND OF THE INVENTION

1. Field of the Invention

The present invention relates to interpenetrating polymer networks wherein one of the components is an acidic polysaccharide or a derivative thereof, a process for their preparation, and their use as biomaterials for biomedical and sanitary applications.

2. Description of Related Art

Hyaluronic acid (HA) is a natural heteropolysaccharide composed of alternate residues of D-glucuronic acid and N-acetyl-D-glucosamine. It is a linear polymer with a molecular weight of between 50,000 and 13,000,000, depending upon the source from which it is obtained and how it is prepared and analyzed. In nature, it is present in pericellular gels, in the fundamental substance of connective tissues in vertebrate organisms, of which it is one of the main components, in the synovial fluid of joints, the vitreous humor, umbilical cord tissues, and in cocks'to combs.

Specific fractions of hyaluronic acid with definite molecular weights are known which do not possess inflammatory activity, and which can therefore be used to facilitate wound healing or to substitute the endobulbar fluids or in therapy for joint pathologies by intra-articular injection, as described in European Patent No. 0 138 572 granted to the present Applicants.

Also known are esters of hyaluronic acid, in which all or part of the carboxy groups of the acid are esterified, and their use in pharmaceuticals and cosmetics, and in biodegradable plastic materials, as described in U.S. Pat. Nos. 4,851,521 and 4,965,353, also granted to the present Applicants.

It is a known fact that the application of hyaluronic acid is able to accelerate healing in patients with bedsores, wounds and burns. Its role in the various stages of wound healing has been described, with the aid of a theoretical model, by Weigel et al. ("A model for the role of hyaluronic acid and fibrin in the early events during the inflammatory response and wound healing," *J. Theor. Biol.*, 119: 219, 1986).

Studies aimed at obtaining products (biomaterials) for medical, sanitary and pharmaceutical applications, composed of hyaluronic acid esters or esters of other polysaccharides used as such or in mixtures with other polymers, have led to the creation of various products. These include tissues such as gauzes of varying density (number of threads per centimeter), of varying dimensions and denier (weight per 9,000 meters of thread), films, membranes, gels, guide channels, etc. Some examples of films appear in two patents granted to the present Applicants, namely U.S. Pat. Nos. 4,851,521 and 4,965,353. The use of such materials is limited by the impossibility of using moulding systems for their construction and use.

An interpenetrating polymer network,. IPN, is an intimate combination of two polymers, both in network form, at least one of which is synthesized or cross-linked in the immediate presence of the other. If one of the two polymers is in network form (crosslinked) and the other is a linear polymer (not crosslinked), a semi-IPN results (L. H. Sperling, Interpenetrating Polymer Networks, CHEMTECH, February, 1988. The term IPN currently covers new materials where the two polymers in the mixture are not necessarily bound together, but the components are physically associated. Clearly, these new materials open up the possibility of giving physical, mechanical and manufacturable properties to easily degradable polymers, creating new materials wherein new biological properties can be coupled with their mechanical properties. Examples of newly-developed IPN and applications thereof have been reported wherein one of the two components is a water-soluble polymer (U.S. Pat. Nos. 4,678,468 and 4,747,953).

IPN comprising a naturally occurring polymer and a synthetic polymer for use in the medical, sanitary, and pharmaceutical areas is, however, novel to the present invention.

SUMMARY OF THE INVENTION

An object of the present invention is to provide a biomaterial, comprising an interpenetrating polymer network, IPN, wherein one of the components is an acidic polysaccharide or a derivative thereof. Said acidic polysaccharide can be hyaluronic acid, and the second polymer component can be a non-toxic, non-carcinogenic synthetic chemical polymer. Said derivative can be a total or partial hyaluronic acid ester or hyaluronic acid salt. Said ester or salt can be formed with a pharmacologically active molecule. Also disclosed are methods for preparing the IPN of the present invention.

Another object of the present invention is to provide IPN wherein said acidic polysaccharide and said synthetic chemical polymer comprising said IPN are crosslinked, or wherein said synthetic chemical polymer is grafted onto said acidic polysaccharide. The crosslinking or grafting can be achieved using compounds capable of generating radicals, or via functional groups on said acidic polysaccharide and said synthetic chemical polymer. Said IPN can be formed prior to crosslinking or grafting, and possess strong interactions between the natural and synthetic polymers therein by virtue of the grafting of the synthetic polymer onto the natural one or the intermolecular crosslinks between the two.

Yet another object of the present invention is to provide said IPN in a form selected from the group consisting of a film, a membrane, a sponge, a hydrogel, a guide channel, a thread, a gauze, and a non-woven tissue.

A further object of the present invention is the use of said IPN in the biomedical and sanitary fields, including their use in dermatology, urology, orthopedics, otologic microsurgery, otoneurology, functional, post-traumatic and rhinosinusal endoscopic microsurgery, plastic surgery, in the cardiovascular system, and in any other type of surgery in which their properties are useful.

The IPN of the present invention possess particular, improved chemical and physical characteristics as compared to conventional IPN. These biomaterials retain the biocompatible characteristics of the polysaccharide, hyaluronic acid, or ester derivative thereof used as one of the two components of the IPN, as well as the mechanical characteristics of the chemical polymer used as the second of the two polymeric components of the IPN.

With respect to the hyaluronic acid esters useful in the present invention, these esters can be used alone or in association with other active principles such as therapeutic agents like antiinfective agents, antibiotics, antimicrobials, antiinflammatory agents, cytostatic agents, cytotoxic agents, antiviral agents, anaesthetic agents, antiseptics, and disinfectants.

With respect to the chemical polymers useful in the present invention, any of those already employed as biomaterials can be used to produce the IPN disclosed infra. Such chemical polymers are described in G. W. Hastings, Macromolecular Biomaterials, CRC Press, 1984, and S. D. Bruck, Properties of Biomaterials in the Physiological Environment, CRC Press, 1980. The only factor limiting the use of such synthetic polymers is that they must be non-toxic and non-carcinogenic.

For purely illustrative purposes, presented below are some examples describing the preparation of IPN according to the present invention.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are incorporated by reference in their entirety.

Preparation of Hyaluronic Acid Fractions Useful in the IPN of the Present Invention

EXAMPLE 1

Method of preparing a mixture of hyalastine and hyalectin having no inflammatory activity Fresh or frozen cocks' combs, (3000 g) are minced in a meat mincer and then carefully homogenized in a mechanical homogenizer. The paste thus obtained is placed in a stainless steel container AISI 316 or in glass and treated with 10 volumes of anhydrous acetone. The whole is agitated for 6 hours at a speed of 50 rpm. It is left to separate for 12 hours and the acetone is discarded by syphoning. The acetone extraction is repeated until the discarded acetone has reached the correct degree of humidity (Karl-Fischer method). The whole is then centrifuged and vacuum dried at a suitable temperature for 5–8 hours. In this way about 500–600 g of dry powdered cocks' combs are obtained.

300 g of dry powder are exposed to enzymatic digestion with papain (0.2 g) under aqueous conditions, buffered with phosphate buffer in the presence of a suitable quantity of cysteine hydrochloride. The resultant is agitated for 24 hours at 60 rpm keeping the temperature constant at 60°–65° C. It is then cooled to 25° C. and Celite® (60 g) is added, maintaining the agitation for another hour. The resulting mixture is filtered until a clear liquid is obtained. The clear liquid then undergoes molecular ultrafiltration using membranes with a molecular exclusion limit of 30,000 in order to retain on the membrane those molecules with a molecular weight greater than 30,000.

The product is ultrafiltered from 5 to 6 original volumes adding distilled water continually to the product in ultrafiltration. The addition of water is suspended and the ultrafiltration is continued until the volume is reduced to ⅓ of the original volume.

The residual liquid is rendered 0.1M by the addition of sodium chloride and the temperature is brought to 50° C. Under agitation at 60 rpm, 45 g of cetylpyridinium chloride are added. It is agitated for 60 minutes and then 50 g of Celite® are added. Under agitation, the temperature of the whole is brought to 25° C. and the precipitate formed by centrifugation is gathered. The precipitate obtained is suspended in a 0.01M solution of sodium chloride (5 liters) containing 0.05% of cetylpyridinium chloride. The resulting suspension is agitated for 60 minutes at 50° C.; the temperature is then brought to 25° C. and the precipitate is centrifuged. The washing operation is repeated 3 times after which the precipitate is gathered in a receptacle containing 3 liters of a 0.05M solution of sodium chloride containing 0.05% of cetylpyridinium chloride. It is agitated at 60 rpm for 60 minutes and the temperature is kept constant at 25° C. for two hours. The supernatant is eliminated by centrifugation. The procedure is repeated several times with solutions of 0.1M sodium chloride containing 0.05% of cetylpyridinium chloride. The mixture is centrifuged and the supernatant is discarded. The precipitate is dispersed in a solution of 0.30M sodium chloride containing 0.05% of cetylpyridinium chloride (3 liters). The mixture is agitated and both the precipitate and the clear liquid are gathered. Extraction is repeated three more times on the precipitate, each time using 0.5 liter of the same aqueous solution.

Finally, the precipitate residue is eliminated and the clear liquids are all placed together in a single container. The temperature of the liquid is brought to 50° C. under constant agitation. The liquid is then brought to 0.23M with sodium chloride. 1 g of cetylpyridinium chloride is added and it is maintained in agitation for 12 hours.

The mixture is cooled at 25° C. and then filtered first on Celite® pack and then through a filter. It then undergoes molecular ultrafiltration again, on a membrane with a molecular exclusion limit of 30,000, ultrafiltering three initial volumes with the addition of a solution of 0.33M sodium chloride. The addition of sodium chloride solution is interrupted and the volume is reduced to ¼ of the initial volume. The solution thus concentrated is precipitated under agitation (60 rpm) at 25° C. with 3 volumes of ethanol (95%). The precipitate is gathered by centrifugation and the supernatant is discarded. The precipitate is dissolved in 1 liter of 0.01M sodium chloride and the precipitation is repeated with 3 volumes of 95% ethanol.

The precipitate is gathered and washed first with 75% ethanol (3 times), then with absolute ethanol (3 times), and lastly with absolute acetone (3 times).

The product thus obtained (HYALASTINE+ HYALECTIN fractions) has an average molecular weight of between 250,000 and 350,000.

The yield of HA is 0.6% of the original fresh tissue.

EXAMPLE 2

Method of preparing the hyalastine fraction from the mixture obtained by the method described in Example 1

The mixture obtained by the method described in Example 1 is dissolved in twice distilled apyrogenic water at the rate of 10 mg of product to each 1 ml of water. The solution obtained is exposed to molecular filtration through filter membranes with a molecular exclusion limit of 200,000, following a concentration technique on the membrane without the addition of water. During the ultrafiltration process through membranes with a molecular exclusion limit of 200,000, the molecules with a molecular weight of more than 200,000 do not pass through, while the smaller molecules pass through the membrane together with the water. During the filtration procedure no water is added, so that the volume decreases, and there is therefore an increase in the concentration of molecules with a molecular weight of more than 200,000. The product is ultrafiltered until the volume on top of the membrane is reduced to 10% of the initial volume. Two volumes of apyrogenic twice distilled water are added and it is then ultrafiltered again until the volume is reduced to ⅓. The operation is repeated twice more. The solution passed through the membrane is brought to 0.1M with sodium chloride and then precipitated with 4 volumes of 95% ethanol. The precipitate is washed 3 times with 75% ethanol and then vacuum dried.

The product thus obtained (HYALASTINE fraction) has an average molecular weight of between 50,000 and 100,000. The yield of HA is equal to 0.4% of the original fresh tissue.

Hyaluronic acid with an average molecular weight of 155,000 can be similarly obtained by employing appropriate ultrafiltration membranes and gel filtration chromatography.

EXAMPLE 3

Method of obtaining the hyalectin fraction

The concentrated solution gathered in the container on top of the ultrafiltration membrane with a molecular exclusion of 200,000 as in Example 2, is diluted with water until a solution containing 5 mg/ml of hyaluronic acid is obtained, as determined by quantitative analysis based on the amount of glucuronic acid.

The solution is brought to 0.1M in sodium chloride and then precipitated with 4 volumes of 95% ethanol. The precipitate is washed 3 times with 75% ethanol and then vacuum dried.

The product thus obtained (HYALECTIN fraction) has an average molecular weight of between 500,000 and 730,000. This corresponds to a specific fraction of hyaluronic acid with a defined molecular chain length of about 2,500 to 3,500 saccharide units with a high degree of purity. The yield of HA is equal to 0.2% of the original fresh tissue.

EXAMPLE 4

Preparation of the tetrabutylammonium salt of hyaluronic acid 4.02 g of HA sodium salt (10 m.Eq.) are solubilized in 400 ml of distilled $H_2O$. The solution is then eluted in a thermostatic column at 4° C. containing 15 ml of sulphonic resin (Dowex 50×8) in tetrabutylammonium form. The eluate, free from sodium, is instantly frozen and freeze-dried. Yield: 6.18 g.

EXAMPLE 5

Preparation of a film of hyaluronic acid (HA) and polyacrylic acid 20 mg of HA (MW 155,000) are dissolved in 2 ml of distilled water by shaking at a temperature of 50° C. for 30 minutes. A 1% solution of HA is thus obtained, which will be referred to as solution A.

80 mg of PAA (MW 250,000) are dissolved in 8 ml of distilled water by shaking at a temperature of 50° C. for 12 hours. A 1% solution of PAA is thus obtained, which will be referred to as solution B1, and this is left to cool to room temperature.

Solution A is slowly added to solution B1 while being continuously shaken at room temperature. Shaking is continued for one hour to allow complete amalgamation of the two components.

The solution containing the mixture of HA/PAA in a weight ratio of 20/80 is poured into a polystyrene Petri dish and placed in a ventilation oven set at 75° C. Once the solvent has evaporated, a transparent and homogeneous film is obtained.

EXAMPLE 6

Preparation of a film of hyaluronic acid (HA) and polyvinylpyrrolidone (PVP)

20 mg of HA (MW 155,000) are dissolved in 2 ml of distilled water by shaking at a temperature of 50° C. for 30 minutes. A 1% solution of HA is obtained, which is referred to as solution A.

80 mg of PVP (MW 40,000) are dissolved in 8 ml of distilled water, by shaking at a temperature of 50° C. for 5 hours. A 1% solution of PVP is obtained, referred to as solution B2, which is left to cool to room temperature.

Solution A is slowly added to solution B2 while shaking at room temperature. The solution is shaken for one hour to allow complete amalgamation of the two components.

The solution containing the mixture of HA/PVP in a weight ratio of 20/80 is poured into a polystyrene Petri dish and placed into a ventilation oven set at a temperature of 75° C. Once the solvent has completely evaporated, a transparent and homogeneous film is obtained.

EXAMPLE 7

Preparation of a film of hyaluronic acid (HA) and polyacrylamide (PAAm)

20 mg of HA (MW 155,000) are dissolved in 2 ml of distilled water, while shaking at a temperature of 50° C. for 30 minutes. A 1% solution of HA is obtained, which will be referred to as solution A.

80 mg of PAAm (MW $5\times10^6$) are dissolved in 8 ml of distilled water, while shaking at a temperature of 50° C. for 12 hours. A 1% solution of PAAm is thus obtained, referred to as solution B3, which is then left to cool to room temperature.

Solution A is slowly added to solution B3 while being continuously shaken at room temperature. The solution is shaken for 1 hour to allow complete amalgamation of the two components.

The solution containing the mixture of HA/PAAm in a weight ratio of 20/80 is poured into a polystyrene Petri dish and placed in a ventilation oven set at 75° C. Once the solvent has completely evaporated, a transparent and homogeneous film is obtained.

EXAMPLE 8

Preparation of a film of hyaluronic acid (HA) and polyethylene oxide (PEO)

20 mg of HA (MW 155,000) are dissolved in 2 ml of distilled water, while shaking at a temperature of 50° C. for 30 minutes. A 1% solution of HA is thus obtained, which will be referred to as solution A.

80 mg of PEO (MW 100,000) are dissolved in 8 ml of distilled water while being shaken at a temperature of 50° C. for 12 hours. A 1% solution of PEO is thus obtained, referred to as solution B4, which is then left to cool to room temperature.

Solution A is slowly poured into solution B4 while being continuously shaken at room temperature. The solution is shaken for one hour to allow complete amalgamation of the two components.

The solution containing the mixture of HA/PEO in a weight ratio of 20/80 is poured into a polystyrene Petri dish and placed in a ventilation oven at a temperature of 75° C. Once the solvent has completely evaporated, a transparent and homogeneous film is obtained.

EXAMPLE 9

Preparation of a film of hyaluronic acid (HA) and Mowiol (vinyl alcohol-vinyl acetate copolymer, MOW)

20 mg of HA (MW 155,000) are dissolved in 2 ml of distilled water while being shaken at a temperature of 50° C. for 30 minutes. A 1% solution of HA is obtained, which will be referred to as solution A.

80 mg of MOW (MW 127,000) are dissolved in 8 ml of distilled water, while being shaken at a temperature of 50° C. for 12 hours. A 1% solution of MOW is thus obtained, referred to as solution B5, which is then left to cool to room temperature.

Solution A is slowly added to solution B5 while being continuously shaken at room temperature. The solution is shaken for 1 hour to allow complete amalgamation of the two components.

The solution containing the mixture of HA/MOW in a weight ratio of 20/80 is poured into a polystyrene Petri dish and placed in a ventilation oven set at a temperature of 75° C. Once the solvent has completely evaporated, a transparent and homogeneous film is obtained.

EXAMPLE 10

Preparation of a film of hyaluronic acid (HA) and polyvinyl alcohol (PVA)

20 mg of HA (MW 155,000) are dissolved in 2 ml of distilled water, while shaking at a temperature of 50° C. for 30 minutes. A 1% solution of HA is thus obtained, which will be referred to as solution A.

80 mg of PVA (MW 115,000) are placed in a flask, with a reflux cooling system and a magnetic stirrer, containing 8 ml of distilled water. The flask is placed in an oil bath at a temperature of 150° C. and shaken for 5 hours. Once the PVA has completely dissolved, a 1% solution of PVA is obtained, which will be referred to as solution B6; this is left to cool to room temperature.

Solution A is slowly added to solution B6 under constant shaking at room temperature. The solution is shaken for 1 hour to allow complete amalgamation of the two components.

The solution containing the mixture of HA/PVA in a weight ratio of 20/80 is poured into a polystyrene Petri dish and placed in a ventilation oven set at a temperature of 75° C. Once the solvent has completely dissolved, a transparent and homogeneous film is obtained.

EXAMPLE 11

Preparation of a film of hyaluronic acid (HA) and polyphosphazenes, for example poly-(trifluoroethoxy) phosphazene (PF1)

20 mg of HA (MW 155,000) are dissolved in 2 ml of distilled water while being shaken at a temperature of 50° C. for 30 minutes. A 1% solution of HA is thus obtained, which will be referred to as solution A. 80 mg of PF1 (MW 15,000) are dissolved in 8 ml of distilled water while being shaken at a temperature of 50° C. for 12 hours. A 1% solution of PFI is thus obtained, which will be referred to as solution B7; this is left to cool to room temperature.

Solution A is slowly added to solution B7 while being constantly shaken at room temperature. The solution is shaken for one hour to allow complete amalgamation of the two components.

The solution containing the mixture of HA/PFI in a weight ratio of 20/80 is poured into a polystyrene Petri dish and placed in a ventilation oven set at a temperature of 75° C. Once the solvent has completely evaporated, a transparent and homogeneous film is obtained.

EXAMPLE 12

Preparation of a film of hyaluronic acid (HA) and polyphosphazenes, for example poly-(di(p-sodio sulfoxy phenoxy)phosphazene (PF2)

20 mg of HA (MW 155,000) are dissolved in 2 ml of distilled water while being shaken at a temperature of obtained, which will be referred to as solution A.

80 mg of PF2 (MW 15,000) are dissolved in 8 ml of distilled water while being shaken at a temperature of 50° C. for 5 hours. A 1% solution of PF2 is thus obtained, which will be referred to as solution B8; this is left to cool to room temperature.

Solution A is slowly added to solution B8 while being continuously shaken at room temperature. The solution is shaken for one hour to allow complete amalgamation of the two components.

The solution containing the mixture of HA/PF2 in a weight ratio of 20/80 is poured into a polystyrene Petri dish and placed in a ventilation oven set at a temperature of 75° C. Once the solvent has completely evaporated, a transparent and homogeneous film is obtained.

The following examples illustrate the preparation of sponges by the freeze-drying of mixtures of hyaluronic acid and water-soluble polymers.

EXAMPLE 13

Preparation of a freeze-dried sponge containing hyaluronic acid (HA) and polyacrylic acid (PAA)

20 mg of HA (MW 155,000) are dissolved in 2 ml of distilled water while being shaken at a temperature of 50° C. for 30 minutes. A 1% solution of HA is thus obtained, which will be referred to as solution A, and which is left to cool to room temperature.

80 mg of PAA (MW 250,000) are dissolved in 8 ml of distilled water, while being shaken at a temperature of 50° C. for 12 hours. A 1% solution of PASA is thus obtained, referred to as solution B1, which is left to cool to room temperature.

Solution A is slowly added to solution B1 while shaking at room temperature. The solution is shaken for 1 hour to allow complete amalgamation of the two components.

The solution containing the mixture of HA/PAA in a weight ratio of 20/80 is poured into a polystyrene Petri dish and placed in a freeze-drier. Lyophilization is achieved by freezing to −30° C. at atmospheric pressure, then heating to −20° C. in a vacuum (0.015 mbar) for 24 hours. Once the freeze-drying process is complete, a soft, white, spongy material is obtained.

EXAMPLE 14

Preparation of a freeze-dried sponge containing hyaluronic acid (HA) and polyvinylpyrrolidone (PVP)

20 mg of HA (MW 155,000) are dissolved in 2 ml of distilled water at a temperature of 50° C. for 30 minutes. A 1% solution of HA is obtained, which will be referred to as solution A; this is left to cool no room temperature.

80 mg of PVP (MW 40,000) are dissolved in 8 ml of distilled water while being shaken at a temperature of 50° C. for 12 hours. A 1% solution of PVP is thus obtained which will be referred to as solution B2; this is left to cool to room temperature.

Solution A is slowly added to solution B2 while being constantly shaken at room temperature. The solution is shaken for 1 hour to allow complete amalgamation of the two components.

The solution containing the mixture of HA/PVP in a weight ratio of 20/80 is poured into a polystyrene Petri dish and placed in a freeze-drier. Lyophilization is achieved by freezing to −30° C. at atmospheric pressure, then heating to −20° C. in a vacuum (0.015 mbar) for 24 hours. Once the freeze-drying process is complete, a soft, white, spongy material is obtained.

EXAMPLE 15

Preparation of a freeze-dried sponge containing hyaluronic acid (HA) and polyacrylamide (PAAm)

20 mg of HA (MW 155,000) are dissolved in 2 ml of distilled water while being shaken at a temperature of 50° C. for 30 minutes. A 1% solution of HA is thus obtained, which will be referred to as solution A; this is left to cool to room temperature.

80 mg of PAAm (MW $5\times10^6$) are dissolved in 8 ml of distilled water while being shaken at a temperature of 50° C. for 12 hours. A 1% solution of PAAm is thus obtained, which will be referred to as solution B3; this is left to cool to room temperature.

Solution A is slowly added to solution B3 while being continually shaken at room temperature. The solution is shaken for 1 hour to allow complete amalgamation of the two components.

The solution containing the mixture of HA/PAAm in a weight ratio of 20/80 is poured into a polystyrene Petri dish and placed in a freeze-drier. Lyophilization is achieved by freezing to −30° C. at atmospheric pressure, and then heating to −20° C. in a vacuum (0.015 mbar) for 24 hours. Once the freeze-drying process is complete a soft, white, spongy material is obtained.

EXAMPLE 16

Preparation of a freeze-dried sponge containing hyaluronic acid (HA) and polyethylene oxide (PEO)

20 mg of HA (MW 155,000) are dissolved in 2 ml of distilled water while being shaken at a temperature of 50° C. for 30 minutes. A 1% solution of HA is thus obtained, which will be referred to as solution A; this is left to cool to room temperature.

80 mg of PEO (MW 100,000) are dissolved in 8 ml of distilled water while being shaken at a temperature of 50° C. for 12 hours. A solution referred to as B4 is obtained; this is left to cool to room temperature.

Solution A is slowly added to solution B4 while being continuously shaken at room temperature. The solution is shaken for 1 hour to allow complete amalgamation of the two components.

The solution containing the mixture of HA/PEO in a weight ratio of 20/80 is poured into a polystyrene Petri dish and placed in a freeze-drier. Lyophilization is achieved by freezing to −30° C. at atmospheric pressure, and then heating to −20° C. in a vacuum (0.015 mbar) for 24 hours. Once the freeze-drying process is complete, a soft, white, spongy material is obtained.

EXAMPLE 17

Preparation of a freeze-dried sponge containing hyaluronic acid (HA) and polyphosphazenes, for example poly (methoxy ethoxy)phosphazene (PF3)

20 mg of HA (MW 155,000) are dissolved in 2 ml of distilled water while being shaken at a temperature of 50° C. for 30 minutes. A 1% solution of HA is thus obtained, which will be referred to as solution A; this is left to cool to room temperature.

80 mg of PF3 (MW 15,000) are dissolved in 8 ml of distilled water while being shaken at a temperature of 50° C. for 12 hours. A 1% solution of PF3 is thus obtained, which will be referred to as solution B5; this is left to cool to room temperature.

Solution A is slowly added to solution B5 while being shaken at room temperature. The solution is shaken for one hour to allow complete amalgamation of the two components.

The solution containing the mixture of HA/PF3 in a weight ratio of 20/80 is poured into a polystyrene Petri dish and placed in a freeze-drier. Lyophilization is achieved by freezing to −30° C. at atmospheric pressure, followed by heating to −20° C. in a vacuum for 24 hours. Once the freeze-drying process is complete, a soft, white, spongy material is obtained.

EXAMPLE 18

Preparation of a hydrogel containing hyaluronic acid (HA) and polyvinyl alcohol (PVA) 20 mg of HA (MW 155,000) are dissolved in 2 ml of distilled water while being shaken at a temperature of 50° C. for 30 minutes. A 1% solution of HA is obtained, which will be referred to as solution A.

320 mg of PVA (MW 115,000) are placed in a flask, with a reflux cooling system and a magnetic stirrer, containing 8 ml of distilled water. The flask is placed in an oil bath at a temperature of 150° C. for 5 hours while being shaken. Once the PVA has completely dissolved, a 4% solution of PVA is obtained, which will be referred to as solution B6; this is left to cool to room temperature.

Solution A is slowly added to 2 ml of solution B6 while being constantly shaken at room temperature. The solution containing the mixture of HA/PVA in a weight ratio of 20/80 is shaken for one hour to allow complete amalgamation of the two components.

The solution of HA/PVA is poured into a polystyrene Petri dish and exposed to 5 freeze-thaw cycles. Each cycle consists of bringing the sample from room temperature to −20° C., keeping the sample at this temperature for one hour, thawing it by bringing it back to room temperature, and completing the cycle by keeping it at room temperature for one hour.

By the second cycle, the solution already has a gelatinous appearance, and its consistency increases with subsequent cycles. At the end of the fifth cycle, the sample has a uniform, white, rubbery consistency, and its water content is about 60%.

The following examples illustrate the preparation of films by the evaporation of the solvent from mixtures of hyaluronic acid (HA) dissolved in dimethyl sulfoxide (DMSO) and polymers soluble in DMSO.

EXAMPLE 19

Preparation of a film containing hyaluronic acid (HA1) and polyvinyl alcohol (PVA) HA is dissolved in DMSO as follows: 100 mg of HA (MW 155,000) are dissolved in distilled water while being shaken at room temperature for 30 minutes. The water is then substituted with DMSO by adding the second solvent to the solution and heating to 90° C. to evaporate the water. Further DMSO is added to bring the solution to a final volume of 10 ml. A 1% solution of HA in DMSO is thus obtained, which will be referred to as solution A in Examples 15–17.

100 mg of PVA are dissolved in DMSO while being shaken at a temperature of 100° C. for 1 hour and then brought to a final volume of 10 ml. A 1% solution of PVA is thus obtained, which will be referred to as solution B. Solution A is slowly added to solution B while being continuously shaken at a temperature of 100° C. The resulting solution is shaken for one hour to allow complete amalgamation of the two components.

The resulting solution containing the mixture of HA/PVA in a weight ratio of 20/80 is poured into a polystyrene Petri dish and placed in a ventilation oven set at a temperature of 75° C. Once the solvent has completely evaporated, a transparent, homogeneous film is obtained.

EXAMPLE 20

Preparation of a film containing hyaluronic acid (HA) and Clarene L6, Solvay (Cl L6), ethylene-vinyl alcohol copolymer with a low ethylene content (29 mole %) 5 100 mg of Cl L6 are dissolved in DMSO while shaking for 1 hour and brought to a final volume of 10 ml. A 1% solution of Cl L6 is obtained, which will be referred to as solution C.

Solution A is slowly added to solution C while being continuously shaken at a temperature of 70° C. The resulting solution is shaken for 1 hour to allow complete amalgamation of the two components.

The resulting solution containing the mixture of HA/Cl L6 in a weight ratio of 20/80 is poured into a polystyrene Petri dish and placed in a ventilation oven set at a temperature of 75° C. Once the solvent has completely evaporated, a transparent and homogeneous film is obtained.

EXAMPLE 21

Preparation of a film containing hyaluronic acid (HA) and Clarene P10, Solvay (Cl P10), ethylene-vinyl alcohol copolymer with a medium ethylene content (36 mole %)

100 mg of Cl P10 are dissolved in DMSO while being shaken at a temperature of 70° C. for one hour and then brought to a final volume of 10 ml. A 1% solution of Cl P10 is thus obtained, which will be referred to as solution D.

Solution A is slowly added to solution D while being continuously shaken at a temperature of 70° C. The resulting solution is shaken for one hour to allow complete amalgamation of the two components.

The resulting solution containing the mixture of HA/Cl P10 in a weight ratio of 20/80 is poured into a polystyrene Petri dish and placed in a ventilation oven set at a temperature of 75° C. Once the solvent has completely evaporated, a transparent and homogeneous film is obtained.

EXAMPLE 22

Preparation of a film containing hyaluronic acid (HA) and Clarene R20, Solvay (Cl R20), ethylene-vinyl alcohol copolymer with a high ethylene content (40 mole %)

100 mg of Cl R20 are dissolved in DMSO while being shaken at a temperature of 70° C. for one hour and brought to a final volume of 10 ml. A 1% solution of Cl R20 is thus obtained, which will be referred to as solution E.

Solution A is slowly added to solution E under continuous shaking at a temperature of 70° C. The resulting solution is shaken for one hour to allow complete amalgamation of the two components.

The solution containing the mixture of HA/Cl R20 in a weight ratio of 20/80 is poured into a polystyrene Petri dish and placed in a ventilation oven set at a temperature of 75° C. Once the solvent has completely evaporated, a transparent and homogeneous film is obtained.

EXAMPLE 23

Preparation of a film containing hyaluronic acid (HA) and polyurethane (PU), Cardiomat 610, Contron 0.670 ml, of a 15% solution of PU in tetrahydrofuran:dioxan, 1:1, are dissolved in 8 ml of DMSO while being shaken at a temperature of 70° C. for one hour. When the starting solvents have evaporated, the solution is brought to a final volume of 10 ml with DMSO. A 1% solution of PU is thus obtained, which will be referred to as solution F.

Solution A is slowly added to solution F while being continuously stirred at a temperature of 70° C. The resulting solution is shaken for one hour to allow complete amalgamation of the two components.

The resulting solution containing HA/PU in a weight ratio of 20/80 is poured into a polystyrene Petri dish and placed into a ventilation oven set at 75° C. Once the solvent has completely evaporated, a transparent and homogeneous film is obtained.

EXAMPLE 24

Preparation of a film containing hyaluronic acid (HA) and polylactic acid (PLA)

100 mg of PLA are dissolved in DMSO while being shaken at a temperature of 85° C. for one hour and then brought to a final volume of 10 ml. A 1% solution of PLA is thus obtained, which will be referred to as solution G.

Solution A is slowly added to solution G while being continuously shaken at a temperature of 85° C. The resulting solution is shaken for one hour to allow complete amalgamation of the two components.

The resulting solution, containing the mixture of HA/PLA in a weight ratio of 20/80 is poured into a polystyrene Petri dish and placed in a ventilation oven set at a temperature of 75° C. Once the solvent has completely evaporated, a transparent and homogeneous film is obtained.

Use of Hyaluronic Ester Derivatives in IPN

The present IPN can be prepared using not only hyaluronic acid, but ester derivatives of hyaluronic acid as well. The preparation of such esters is described in U.S. Pat. No. 4,851,521.

Ester derivatives of hyaluronic acid useful in the present invention are esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters include esters which derive from alcohols which themselves possess a notable pharmacological action. The saturated alcohols of the aliphatic series or simple alcohols of the cycloaliphatic series are useful in the present invention.

In the above-mentioned esters in which some of the carboxylic acid groups remain free (i.e., partial esters), these may be salified with metals or organic bases, such as with alkaline or alkaline earth metals or with ammonia or nitrogenous organic bases.

Alcohols of the aliphatic series to be used as esterifying components of the carboxylic groups of hyaluronic acid for use in the IPN according to the present invention are, for example, those with a maximum of 14 carbon atoms, which may be saturated or unsaturated, and which may possibly also be substituted with other free functional or functionally modified groups, such as amine, hydroxyl, aldehyde, ketone, mercaptan, or carboxyl groups, or by groups derived from these, such as hydrocarbyl or di-hydrocarbylamine groups (the term "hydrocarbyl" refers not only to monovalent radicals of hydrocarbons such as the $C_nH_{2n+1}$ type, but also bivalent or trivalent radicals, such as "alkylenes," $C_nH_{2n}$, or "alkylidenes," $C_nH_{2n}$, ether or ester groups, acetal or ketal groups, thioether or thioester groups, and esterified carboxyl or carbamide groups and carbamide substituted with one or more hydrocarbyl groups, with nitrile groups, or with halogens.

Of the above-mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above-mentioned group which are preferably used are those with a maximum of 14, and especially 6 carbon atoms, and in which the hydrocarbyl atoms in the above-mentioned amine, ether, ester, thioether, thioester, acetal, or ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups may be alkylenamine or alkylencarbamide groups with a maximum of 8 carbon atoms. Of these alcohols, specifically preferred are saturated and non-substituted alcohols, such as methyl, ethyl, propyl, and isopropyl alcohols, normal butyl alcohol, isobutyl alcohol, tertiary butyl alcohol, amyl, pentyl, hexyl, octyl, nonyl and dodecyl alcohols, and those with a linear chain, such as normal octyl and dodecyl alcohols. Of the substituted alcohols of this group, the bivalent alcohols are ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidinylethanol, piperazineylethanol and the corresponding derivatives of normal propyl or normal butyl alcohol, monothioethyleneglycol or its alkyl derivatives, such as the ethyl derivative in the mercaptan function, are useful.

Of the higher saturated aliphatic alcohols, preferred are cetyl alcohol and myricyl alcohol, but for the aim of the present invention, the higher unsaturated alcohols with one or two double bonds are especially important, such as especially those contained in many essential oils and with affinity to terpene, such as citronellol, geraniol, nerol, nerolidol, linalool, farnesol, and phytol. Of the unsaturated lower alcohols, it is necessary to consider allyl alcohol and propargyl alcohol. Of the araliphatic alcohols, preferred are those with only one benzene residue and in which the aliphatic chain has a maximum of 4 carbon atoms, where the benzene residue can be substituted by between 1 and 3 methyl or hydroxyl groups or by halogen atoms, especially by chlorine, bromine and iodine, and in which the aliphatic chain may be substituted by one or more functions chosen from the group containing free amine groups or mono- or dimethylated, or by pyrrolidine or piperidine groups. Of these alcohols, most preferred are benzyl alcohol and ethyl alcohol.

The alcohols of the cycloaliphatic or aliphatic-cycloaliphatic series may derive from mono- or polycyclic hydrocarbons, may preferably have a maximum of 14 carbon atoms, may be unsubstituted, and may contain one or more substituents, such as those mentioned above for the aliphatic alcohols. Of the alcohols derived from cyclic monoannular hydrocarbons, preferred are those with a maximum of 12 carbon atoms, the rings with preferably between 5 and 7 carbon atoms, which may be substituted, for example, with between one and three lower alkyl groups, such as methyl, ethyl, propyl or isopropyl groups. As specific alcohols of this group, the following are most preferred: cyclohexanol, cyclohexanediol, 1,2,3-cyclohexanetriol, and 1,3,5-cyclohexanetriol (phloroglucitol), inositol, and the alcohols which derive from p-methane such as carvomenthol, menthol, and α-γ terpineol, 1-terpineol, 4-terpineol and piperitol, or the mixture of these alcohols known as "terpineol", 1,4- and 1,8-terpin. Of the alcohols which derive from hydrocarbons with condensed rings, such as those of thujane, pinane or comphane, the following are preferred: thujanol, sabinol, pinol hydrate, D- and L-borneol, and D- and L-isoborneol.

Aliphatic-cycloaliphatic polycyclic alcohols to be used for the esters of the present invention include sterols, cholic acids, and steroids, such as sexual hormones and their synthetic analogues, especially corticosteroids and their derivatives. It is therefore possible to use cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin, and their alkylate derivatives, as well as their ethynyl or propynyl derivatives in position 17, such as 17α-ethynl-estradiol or 7α-methyl -17α-ethynyl-estradiol, pregnenolone, pregnanediol, testosterone and its derivatives, such as 17α-methyltestosterone, 1,2 -dehydrotestosterone and 17α-methyl-1,2-dehydrotesterone, the alkynylate derivatives in position 17 of testosterone and 1,2-dehydrotestosterone, such as 17α-ethynyltestosterone, 17α-propynyltestosterone, norgestrel, hydroxyprogesterone, corticosterone, deoxycorticosterone, 19-nortestosterone, 19-nor-17α-methyltestosterone and 19-nor-17α-ethynyltestosterone, antihormones such as cyproterone, cortisone, hydrocortisone, prednisone, prednisolone, fluorocortisone, dexamethasone, betamethasone, paramethasone, flumethasone, fluocinolone, fluprednylidene, clobetasol, beclomethasone, aldosterone, deoxycorticosterone, alfaxolone, alfadolone, and bolasterone. As esterifying components for the esters of the present invention the following are useful: genins (aglycons) of the cardioactive glucosides, such as digitoxigenin, gitoxigenin, digoxigenin, strophanthidin, tigogenin and saponins.

Other alcohols to be used according to the present invention are the vitamin ones, such as axerophthol, vitamins $D_2$ and $D_3$, aneurine, lactoflavine, ascorbic acid, riboflavine, thiamine, and pantothenic acid.

Of the heterocyclic acids, the following can be considered as derivatives of the above-mentioned cycloaliphatic or aliphatic-cycloaliphatic alcohols if their linear or cyclic chains are interrupted by one or more, for example by between one and three heteroatoms, for instance chosen from the group formed by —O—, —S—, —N, and —NH—, and in these, there may be one or more unsaturated bonds, for example double bonds, in particular between one and three, thus including also heterocyclic compounds with aromatic structures. For example, the following should be mentioned: furfuryl alcohol, alkaloids and derivatives such as atropine, scopolamine, cinchonine, 1a cinchonidine, quinine, morphine, codeine, nalorphine, N-butylscopoiammonium bromide, ajmaline; phenylethylamines such as ephedrine, isoproterenol, epinephrine; phenothiazine drugs such as perphenazine, pipothiazine, carphenazine, homofenazine, acetophenazine, fluophenazine, and N-hydroxyethylpromethazine chloride; thioxanthene drugs such as flupenthixol and clopenthixol; anticonvulsants such as meprophendiol; antipsychotics such as opipramol; antiemetics such as oxypendyl; analgesics such as carbetidine and phenoperidine and methadol; hypnotics such as etodroxizine; anorexics such as benzidrol and diphemethoxidine; minor tranquilizers such as hydroxyzine; muscle relaxants such as cinnamedrine, diphylline, mephenesin, methocarbamol, chlorphenesin, 2,2-diethyl-1, 3-propanediol, guaifenesin, hydrocilamide; coronary vasodilators such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antibiotics such as chloramphenicol, thiamphenicol, erythromycin, oleandomycin, and lincomycin; antivirals such as idoxuridine; peripheral vasodilators such as isonicotinyl alcohol; carbonic anhydrase inhibitors such as sulocarbilate; antiasthmatic and antiinflammatories such as tiaramide; and sulfamidics such as 2-p-sulfanilonoethanol.

In some cases, hyaluronic acid esters may be of interest where the ester groups derive from two or more therapeutically active hydroxylic substances, and naturally all possible variants may be employed. Especially interesting are the substances in which two types of different ester groups deriving from drugs of a hydroxylic character are present, and in which the remaining carboxyl groups are free, salified with metals, or with a base, possibly also the bases being themselves therapeutically active, for example with the same or similar activity as that of the esterifying component. In particular, it is possible to use hyaluronic esters deriving on the one hand from an antiinflammatory steroid, such as one of those mentioned previously, and on the other hand from a vitamin, from an alkaloid, or from an antibiotic, such as one of those listed.

EXAMPLE 25

Methods of preparing the hyaluronic acid esters of the present invention
Method A:

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents, it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluenesulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane or aprotic solvents, such as dimethyl-sulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or accordingto the other procedure described hereafter, free carboxylic groups of the partial esters may be salified, if desired, in a per se known manner.

Method B:

The hyaluronic esters may also be prepared by a method which consists of treating a quaternary ammonium salt of hyaluronic acid with an etherifying agent, preferably in an aprotic organic solvent.

As organic solvents it is preferable to use aprotic solvents, such as dialkylsulphoxides, dialkylcarboxamides, such as in particular lower alkyl dialkylsulphoxides, especially dimethyl-sulphoxide, and lower alkyl dialkylamides of lower aliphatic acids, such as dimethyl or diethyl-formamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethyl-sulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially sodium or potassium salt, in aqueous solution with a salified sulphonic resin with a quaternary ammonium base.

One variation of the previously described procedure consists in reacting a potassium or sodium salt of hyaluronic acid, suspended in a suitable solution such as dimethylsulphoxide, with a suitable alkylating agent in the presence of catalytic quantities of a quaternary ammonium salt, such as iodide of tetrabutylammonium.

In the partial esters of the invention the non-esterified carboxylic groups may be kept free or may be salified. For the formation of such salts the bases are chosen according to the criterion of these for which the product is intended. It is possible to form inorganic salts deriving from alkaline metals, such as potassium and especially sodium and ammonium, or deriving from alkaline earth metals, such as calcium, or magnesium or aluminum salts.

Particularly interesting are the salts with organic bases, especially nitrogenized bases and therefore aliphatic, arylaliphatic, cycloaliphatic or heterocyclic amines.

These ammonia salts may derive from therapeutically acceptable but inactive amines or from amines with therapeutic action. Of the former the aliphatic amines above all should be considered, such as mono-, di- and tri-alkylamines with alkyl groups having a maximum of 18 carbon atoms or arylalkylamines with the same number of carbon atoms in the aliphatic part and where aryl means a benzene group possibly substituted by 1 and 3 methyl groups or halogen atoms or hydroxyl groups. The biologically inactive bases for the formation of salts may also be cyclic such as monocyclic alkylenamines with cycles of between 4 and 6 carbon atoms, possible interrupted in the cycle by heteroatoms chosen from the group formed by nitrogen, oxygen and sulfur, such as piperidine or morpholine, and may be substituted for example by aminic or hydroxylic functions, such as aminoethanol, ethylendiamine, ephedrine or choline.

It is also possible to form the quaternary ammonium salts of the partial esters, for example the salts of tetraalkylammonium with the above-mentioned number of carbon atoms and preferably salts of such a type in which the fourth alkyl group has between 1 and 4 carbon atoms, for example a methyl group.

Among the biologically active amines whose therapeutic actions may be put to use, are included all the nitrogenized and basic drugs such as those included in the following groups: alkaloids, peptides, phenothiazines, benzodiazepines, thioxanthenes, hormones, vitamins, anticonvulsants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, nonsteroid antiinflammatory agents, vasoconstrictors, cholinergic agonists, cholinergic antagonists, adrenergic agonists, adrenergic antagonists, and narcotic antagonists.

All those drugs with basic nitrogenized groups listed in the invention and regarding the use of the esters may be quoted as examples.

According to a particular aspect of the present invention the hyaluronic esters and their salts may be used as an excellent vehicle for therapeutically active substances. To this end it is possible to use the total esters or the partial esters of the salified partial esters in the remaining carboxylic groups, for example with one of the above-mentioned substances therapeutically acceptable but not biologically active, above all with alkaline metals, for example sodium. These are the above-mentioned medicaments made by association containing two components:

Component (1)—a pharmacologically active substance or an association of two or more active substances; and Component (2)—a carrying vehicle comprising a partial or total ester of hyaluronic acid with an alcohol, or the salts of such partial esters with an organic or inorganic base, optionally with the addition of hyaluronic acid or a salt thereof with an inorganic or organic base.

The hyaluronic esters to be used in these medicaments are above all those in which the esterifying alcohol is not pharmacologically active, for example a simple aliphatic alcohol, as described above. Medicaments of this type in which the ester also is pharmacologically active, for example a simple aliphatic alcohol, as described above. Medicaments of this type in which the ester also is pharmacologically active are not excluded from this aspect of the invention, as for example in the case of one of the esters described above deriving from alcohols with pharmacological action.

In the same way, the invention also includes medicaments of this type in which the esters of Component (2) are salified also with therapeutically active bases. These bases maybe the same pharmacologically active substances vehicled in the hyaluronic ester, and the mixture in this case, as describe below, therefore contains salts of a partial ester of hyaluronic acid with therapeutically active bases, possibly in the presence of an excess of active base component (1). The case may on the other hand present itself where the vehicled substance is not of a basic nature, and free carboxylic groups in the hyaluronic ester are still salified with therapeutically active bases.

The use of hyaluronic esters as a vehicle allows therefore the preparation of the medicaments described above, including (1) a pharmacologically active substance or an association of two or more of such substances and (2) a hyaluronic ester as described above or one of its salts. In such medicaments, if partial esters of HA are used, the possible salification of the uremaining carboxylic groups is carried out preferably with therapeutically neutral inorganic or organic bases, especially with alkaline metals such as sodium or ammonium. Should the active substance component (1) or a corresponding association of substances have basic groups, such as for example antibiotics containing amine groups, and if partial esters of hyaluronic acid should be used with remaining free carboxylic groups, the corresponding salts are formed between the carboxylic groups and these basic substances. The new medicaments therefore include in particular partial esters of hyaluronic acid partially and totally salified with pharmacologically active substances and of a basic character. As described above, particularly important are the associated medicaments of the type described herein, in which Component (1) is a pharmacologically active substance for topical use.

The use of hyaluronic esters as a vehicle for drugs to be applied topically is particularly useful in ophthalmology where a particular compatibility is to be observed for the products with the corneal epithelium, and therefore excellent tolerability, without any sensitization effects. Furthermore, when the medicaments are administered in the form of concentrated solutions with elastic-viscose characteristics or in solid form, it is possible to achieve homogenous and stable films which are perfectly transparent and adhesive on the corneal epithelium, guaranteeing prolonged bioavailability of the drug and therefore representing excellent preparations with a retard effect.

Such ophthalmic medicaments are particularly valuable in the veterinary field, considering for example that at present there are no veterinary specialties for oculistic use containing chemotherapeutic agents. Indeed, preparations intended for human use are usually used, and these do not always guarantee a specific range of action or they do not make allowances for the particular conditions in which the treatment must take place. This, for example, is the case in therapy for infectire kerato-conjunctivities, pink eye or IBK, an infection which usually affects cattle, sheep and goats. Presumably for these three species there are specific etiological factors and more particularly: in cattle the main microorganism involved seems to be *Moraxella boris* (even though other agents of a viral origin should not be excluded, such as for example *Rinotracheitis virus*, in sheep Micoplasma, Rickettsiae and Clamidiae, and in goats Rickettsiae). The disease manifests itself in acute form and tends to spread rapidly: in the initial stages the symptomatology is characterized by blepharospasm and excessive lachrymation, followed by purulent exudate, conjunctivities and keratitis, often accompanied by fever, loss of appetite and milk production. Particularly serious are the corneal lesions which in the final stages may even cause perforation of the cornea itself. The clinical progress of the disease varies from a few days to several weeks.

A vast selection of chemotherapeutic agents are used for treatment, administered both topically (often in association with steroid antiinflammatory agents), and systemic, including: tetracyclines, such as oxytetracycline, penicillins, such as cloxacillin and benzylpenicillin, sulfonamides, polymyxin B (associated with miconazole and prednisolone), chloramphenicol, tylosin and ckloromycetin. Topical treatment of the disease, despite its apparent simplicity, is still an unsolved problem, since with the oculistic preparations used so far, it has not been possible for one reason or another, to obtain therapeutically efficient concentrations of antibiotics or sulphamides in the lachrymal secretion. This is quite understandable in the case of solutions, considering the mainly inclined position of the head in these animals, but the same is also true of semisolid medicaments, as the commonly used excipients do not possess the necessary qualities of adhesiveness to the corneal surface, since they do not usually have a high enough concentration of active substance and cannot achieve perfect distribution of the same (i.e., there is a presence of a distribution gradient). These defects of conventional colliriums in ophthalmic use have for example been described by Slatter et al., Austr. Vet. J., 1982, 59(3), pp. 69–72.

With the esters of the present invention these difficulties can be overcome. The presence of the hyaluronic acid ester as a vehicle for ophthalmic drugs in fact allows the formulation of excellent preparations with no concentration gradients of the active substance and they are therefore perfectly homogenous, with perfect transparency and excellent adhesiveness to the corneal epithelium, with no sensitization effects, with excellent vehicling of the active substance and possibly a retard effect.

The above-mentioned properties of the medicaments may of course be exploited also in fields other than ophthalmology. They may be used in dermatology and in diseases of the mucous membranes, for example in the mouth. Furthermore, they may be used to obtain a systemic effect due to the effect of transcutaneous absorption, such as in suppositories,. All these applications are possible both in human and veterinary medicine. In human medicine the new medicaments are particularly suitable for use in pediatrics. The present invention includes therefore in particular any of these therapeutic applications.

For the sake of brevity, from now on when the active substance of component (1) according to the invention is mentioned, it is to be understood to also include the association of one or more active substances.

The component (1) described above may first of all be defined in regard to its use in the various fields of therapy, starting with the distinction between human and veterinary medicine, and then specifying the various sectors of application with regard to the organs or tissues to be treated, such as, with reference to topical use, ophthalmology, dermatology, otorhinolaryngology, gynecology, angiology, neurology, or any type of pathology of internal organs which may be treated with topical applications, for example with rectal applications.

The vehicling action of the hyaluronic esters also applies to associated medicaments of the type mentioned above in which the active substance acts not only topically or by nasal or rectal absorption, for example by nasal sprays or preparations for inhalation for the oral cavity or the pharynx, but also by oral or parenteral route, for example by intramuscular, subcutaneous or intravenous route, as it favors absorption of the drug into the application site. The medicaments can therefore be applied, apart from in the fields already mentioned, in practically all sectors of medicine, such as internal medicine, for example in pathologies of the cardiovascular system, in infections of the respiratory system, the digestive system, the renal system, in diseases of an endocrinological nature, in oncology, in psychiatry, etc., and may also be classified therefore from the point of view of their specific action, being perhaps anesthetics, analgesics, antiinflammatories, wound healers, antimicrobics, adrenergic agonists and antagonists, cytostatics, antirheumatics, antihypertensives, diuretics, sexual hormones, immunostimulants and immunosuppressants, for example, one of the drugs having the activity already described for the therapeutically active alcohols to be used as esterifying component, or for the therapeutically active bases used for the salification of the free carboxylic groups.

Component (1) of the above mentioned medicaments may also be, according to the invention, an association of two or more active substances, as contained in many known medicaments.

Regarding the field of ophthalmology, the indications may be for example: the miotic, antiinflammatory, wound healing and antimicrobial effects.

Examples of pharmacologically active substances to be used in ophthalmic medicaments according to the invention are: basic and non-basic antibiotics such as aminoglycosides, macrolides, tetracyclines and peptides, such as gentamycin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, polymyxin B, gramicidin, colistin, chloramphenicol, lincomycin, vancomycin, novobiocin, ristocetin, clindamycin, amphotericin B, griseofulvin, nystatin, and possibly their salts such as sulfates or nitrates, or associations of the same between themselves or with other active ingredients, such as those mentioned below.

Other ophthalmic drugs to be used to advantage according to the present invention are: other antiinfectives such as diethylcarbamazine, mebendazole, sulfamedics such as sulfacetamide, sulfadiazine, sulfisoxazole, antivirals and antitumorals such as iododeoxyuridine, adenine arabinoside, trifluorothymidine, acyclovir, ethyldeoxyuridine, bromovinyldeoxyuridine, 5-iodo-5'-amino-2',5'-dideoxyuridine; steroid antiinflammatories, such as dexamethasone, hydrocortisone, prednisolone, fluorometholone, medrysone and possibly their esters, for example phosphoric acid; non-steroid antiinflammatories such as indomethacin, oxyphenbutazone, flurbiprofen; wound healers such as epidermal growth factor, EGF; local anesthetics, such as Benoxinate, proparacaine and possibly their salts; cholinergic agonists such as pilocarpine, methcholine, carbomylcholine, aceclidine, physostigmine, neostigmine, demecarium and possibly their salts; cholinergic antagonist drugs such as atropine and their salts; adrenergic agonist drugs such as noradrenaline, adrenaline, naphazoline, methoxamine and possibly their salts; adrenergic antagonist drugs such as propanolol, timolol, pindolol, bupranolol, atenolol, metoprolol, oxprenolol, practolol, butoxamine, sotalol, butathrin, labetolol and possibly their salts.

Examples of the active substances to be used alone or in association among themselves or with other active principles in dermatology are: therapeutic agents such as antiinfective agents, antibiotics, antimicrobials, antiinflammatory, cytostatic, cytotoxic, antiviral, anesthetic agents, and prophylactic agents, such as sun screens, deodorants, antiseptics and disinfectants. Of the antibiotics, particularly important are: erythromycin, bacitracin, gentamicin, neomycin, aureomicin, gramicidin and their associations; of the antibacterials and disinfectants: nitroflurzone, mafenide, chlorhexidine, and derivatives of 8-hydroxyquinoline and possibly their salts; of the antiinflammatory agents, above all the corticosteroids such as prednisolone, dexamethazone, flumethasone, clobetasol, triamcinolone acetonide, betamethasone and their esters, such as valerates, benzoates, dipropionates; of the cytotoxic group: fluorouracil, methotrexate, podophyllin; of the anesthetics, dibucaine, lidocaine, and benzocaine.

This list of course only gives some examples and any other agents described in the literature may be used.

As associations of drugs to be used in dermatology, the various antibiotics should be mentioned, such as erythromycin, gentamycin, neomycin, gramicidin, polymyxin B, among themselves, or associations of these antibiotics with antiinflammatory agents, for example corticosteroids, for example hydrocortisone+neomycin, hydrocortisone+neomycin+polymyxin B+gramicidin, dexamethasone+neomycin, fluorometholone+neomycin, prednisolone+neomycin, triamcinolone+neomycin+ gramicidin+nystatin, or any other association used in conventional preparations for dermatology.

The associations of various active substances are not of course limited to this field, but in each of the above-mentioned areas of medicine it is possible to use associations similar to those already in use for the known pharmaceutical preparations of the art.

In the above case of the use of a component (1) of a basic character, the salts which are formed with a partial hyaluronic ester (since the latter is used to excess) may be of various types, that is, all the remaining carboxylic groups may be salified or only an aliquot part, thereby producing esters-acid salts, or esters-neutral salts. The number of acid groups which are to be kept free may be of importance for the preparation of medicaments with a particular pH. Vice versa, it is possible to use an excess of basic component (1), in which case all the carboxylic groups available in the hyaluronic ester are salified with the base.

According to a particular aspect of the invention it is possible to prepare the medicaments of this type starting from previously isolated and possibly purified salts, in their solid anhydrous state, as amorphous powders, which form an aqueous solution on contact with the tissue to be treated, characterized by viscosity and elastic properties. These qualities are maintained even at stronger dilutions and it is possible therefore to use, in the place of the above-mentioned anhydrous salts, more or less concentrated solutions in water or saline, possibly with the addition of other excipients or additives, such as for example other mineral salts to regulate the pH and osmotic pressure. It is of course possible to use the salts also for the preparation of gels, inserts, creams or ointments, containing also other excipients or ingredients used in traditional formulations of these pharmaceutical preparations.

According to the invention however, the medicaments containing the hyaluronic esters or their salts with therapeutically active or inactive substances as a vehicle are used alone (except possibly with an aqueous solvent). Also included in the invention are the mixtures obtainable from all the types of medicaments described here, mixtures of the same medicaments, and also possibly mixtures of the hyaluronic acid esters with free hyaluronic acid or mixtures of their salts, for example sodium salts.

Component (1) according to the invention may also be associations or mixtures of two or more such drugs and possibly also with other principles. For example, in ophthalmology, a drug may be associated with an antibiotic or antiphlogistic substance and a vasoconstrictor or with several antibiotics, one or more antiphlogistic substances, or with one or more antibiotics, a mydiatric or a miotic or wound healing or antiallergic agent, etc. For example the following associations of ophthamalic drugs may be used: kanamycin+phenylephrine+dexamethasone phosphate; kanamycin+betamethasone phosphate+phenylephrine, or similar associations with other antibiotics used in ophthalmology, such as rolitetracycline, neomycin, gentamicin, and tetracycline.

If in the place of just one active substance component (1) associations of active substances are used, such as those mentioned above, the salts of the basic active substances and the partial ester of hyaluronic acid may be mixed salts of one or more of such basic substances or possibly mixed salts of this type with a certain number of other acid groups of the polysaccharides salified with metals or bases mentioned above. For example, it is possible to prepare salts of a partial ester of hyaluronic acid or of one of the molecular fractions Hyalastine or Hyalectin with a pharmacologically inactive alcohol, for example a lower alkanol and with a certain percentage of salified acid groups with the antibiotic kanamycin, another percentage of carboxylic groups salified with the vasoconstrictor phenylephrine, and a remaining percentage of acid groups may be, for example, free or salified with sodium or one of the other above-mentioned metals. It is also possible to mix this type of mixed salt with free hyaluronic acid or its fractions or their metallic salts, as indicated above-for the medicaments containing salts of one single active substance with the aforementioned polysaccharide esters.

Of the examples discussed for ophthalmology and dermatology it is possible to understand by analogy which medicaments according to the present invention are to be used in the above-mentioned fields of medicine, such as for example in otorhinolaryngology, odontoiogy or in internal medicine, for example in endocrinology. Such preparations may, therefore, be for example antiinflammatories, vasoconstrictors, or vasocompressors such as those already mentioned for ophthalmology, vitamins, antibiotics, such as those mentioned above, hormones, chemiotherapics, antibacterials, etc., also as mentioned above for use in dermatology.

The associated medicaments of a hyaluronic ester with a pharmacologically active substance may contain other pharmaceutical vehicles, such as those mentioned below for the pharmaceutical preparations containing only hyaluronic esters. However, it is preferable to use medicaments containing an association of components (1) and (2), with component (2) as the sole vehicle (apart from a possible solvent such as an aqueous solvent).

Of the medicaments of the invention the following are of particular importance, according to each case, those with a degree of acidity suitable for the environment to which they are to be applied, that is with a physiologically tolerable pH. The adjustment of the for example in the above-mentioned salts of the partial ester of hyaluronic acid with a basic active substance, may be done by suitably regulating the quantities of polysaccharide, of its salts and of the basic substance itself. Thus, for example, if the acidity of a salt of the partial ester of hyaluronic acid with a basic substance is too high, the excess of free acid groups cans be neutralized with the above-mentioned inorganic bases, for example with the hydrate of sodium or potassium or ammonium.

METHOD B

The hyaluronic esters of the present invention may, however, be prepared to advantage according to a second method which may be generally applied to the preparation of carboxylic esters of acidic polysaccharides with carboxyl groups. This method consists of treating a quaternary ammonium salt of an acidic polysaccharide containing carboxyl groups with an etherifying agent, preferably in an aprotic organic solvent.

As organic solvents it is preferable to use aprotic solvents such as dialkylsulphoxides, dialkylcarboxamides, such as in particular lower alkyl diatkylsulphoxides, especially dimethylsulphoxide, and lower alkyl dialkylamides of lower aliphatic acids, such as dimethyl or diethylformamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methytpyrrolidone.

The reaction is effected preferably in a temperature range of between about 0° C. and 100° C., especially between about 25° C. and 75° C., for example at about 30° C.

The esterification is carried out preferably by adding by degrees the esterifying agent to the above-mentioned ammonium salt in one of the above-mentioned solvents, for example to dimethylsulphoxide.

As an alkylating agent it is possible to use those mentioned above, especially the hydrocarbyl halogens, for example alkyl halogens. As starting quaternary ammonium salts it is preferably to use the lower ammonium tetraalkylates, with alkyl groups preferably between 1 and 6 carbon atoms. Mostly, tetrabutylammonium hyaluronate is used. It is possible to prepare these quaternary ammonium salts by reacting a metallic salt of an acidic polysaccharide, preferably one of those mentioned above, especially a sodium or potassium salt, in aqueous solution with a salified sulphonic resin with aa quaternary ammonium base.

The tetraalkylammonium salt of the acidic polysaccharide can be obtained by freeze drying the eluate. The tetraalkylammonium salts of acidic polysaccharides used as starting compounds of the present procedure can derive from inferior alkyls, especially alkyls with between 1 and 6 carbon atoms. Surprisingly, such salts have proved to be soluble in the above-mentioned organic solvents, and for this reason the esterification of acidic polysaccharides according to procedure B is particularly easy and gives generous yields. It is therefore only by using this kind of procedure that one can exactly dose the number of carboxylic groups of acidic polysaccharide which are to be esterified.

One variation of previously described procedure B consists in reacting potassium salt or acidic polysaccharide sodium, suspended in a suitable solution such as dimethylsulphoxide, with a suitable alkylating agent in the presence of catalytic quantities of a quaternary ammonium salt, such as iodide of tetrabutylammonium.

The salification of HA with the above metals, for the preparation of starting salts for the particular esterification procedure of the present invention described above, is performed in a per se known manner, for example by reacting HA with the calculated base quantity, for example with alkaline hydrates or with basic salts of such metals, such as carbonates or bicarbonates.

In the partial esters of the present invention it is possible to salify all the remaining carboxylic groups or only part of them, dosing the base quantities so as to obtain the desired stoichiometric degree of salification. With the correct degree of salification it is possible to obtain esters with a wide range of different dissociation constants and which therefore give the desired pH in solution or in situ at the time of therapeutic application.

Of the products of the present invention, of particular importance are the esters and their salts described above and those described in the following illustrative Examples.

Preparation of Benzyl and Ethyl Esters of Hyaluronic Acid

EXAMPLE 26

Preparation of the total benzyl ester (HYAFF11) of hyaluronic acid 12.4 g of HA tetrabutylammonium salt with a molecular weight of 170,000 corresponding to 20 m.Eq. of a monomeric unit are solubilized in 620 ml of dimethylsulfoxide at 25°. 4.5 g (25 m.Eq.) of benzyl bromide and 0.2 g of tetrabutylammonium iodide are added, and the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30°.

9 g of the benzyl ester product in the title are obtained. Quantitative determination of the ester groups is carried out according to the method described on pages 169–172 of Siggia S. and Hanna J. G., "Quantitative Organic Analysis Via Functional Groups," 4th edition, John Wiley and Sons.

Alternatively, 3 g of the potassium salt of HA with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30°. The resulting mixture is slowly poured into 1,000 ml of ethyl acetate under constant agitation. A precipitate is formed which is filtered and washed four times with 150 ml of ethyl acetate and finally vacuum dried for twenty four hours at 30°.

3.1 g of the benzyl ester product in the title are obtained. Quantitative determination of the ester groups is carried out according to the method described on pages 169–172 of Siggia S. and Hanna J. G., "Quantitative Organic Analysis Via Functional Groups," 4th edition, John Wiley and Sons.

EXAMPLE 27

Preparation of partial benzyl esters (HYAFF 11 p10, p25, p50, and p75) of hyaluronic acid The partial benzyl esters of hyaluronic acid, HYAFF 11 p10, p25, p50, and p75, can be prepared as described in Method B, supra. The esterification can be carried out by adding by degrees the esterifying agent to the quaternary ammonium salt of hyaluronic acid treated with an etherifying agent in an appropriate organic solvent.

The salification of hyaluronic acid for the preparation of starting salts for esterification and the salification of the remaining carboxyl groups in the partial benzyl esters is also described in Method B.

EXAMPLE 28

Preparation of the ethyl ester (HYAFF 7) of hyaluronic acid 12.4 g of HA tetrabutylammonium salt with a molecular weight of 85,000 corresponding to 20 m.Eq. of a monomeric unit are solubilized in 620 ml of dimethylsulfoxide at 25°. 3.3 g (21.2 m.Eq.) of ethyl iodide are added and the solution is kept for 12 hours at 30°.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30°.

8 g of the ethyl ester product in the title are obtained. Quantitative determination of the ester groups is carried out using the method of R. H. Cundiff and P. C. Markunas, Anal. Chem. 33, 1028–1030, (1961).

EXAMPLE 29

Preparation of the (partial) cortisone ester ($C_{21}$) of hyaluronic acid (HA)-20% of esterified carboxylic groups-80% of salified carboxylic groups (Na)

6.2 g of HA tetrabutylammonium salt with a molecular weight of 105,000 corresponding to 10 m.Eq of a monomeric unit are solubilized in 310 ml of dimethylsulfoxide at 25°. 0.850 g (2 m.Eq) of 21-bromo-4-pregnene-17α-ol-3, 11,20-trione are added and the resulting solution is kept for 24 hours at 30°.

A solution containing 100 ml of water and 5 g of sodium chloride is added and the resulting mixture is slowly poured into 2,000 ml of acetone under constant agitation. A precipitate is formed which filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.5 g of the partial cortisone ester compound in the title are obtained. Quantitative determination of cortisone, after mild alkaline hydrolysis with a hydroalcoholic solution of $Na_2CO_3$ and extraction with chloroform, is carried out according to British Pharmacopea, 1980, P. 127.

EXAMPLE 30

Preparation of the (partial) hydrocortisone ester ($C_{21}$) of hyaluronic acid (HA)-20% of esterified carboxylic groups-80% of salified carboxylic groups (Na)

6.2 g of HA tetrabutylammonium salt with a molecular weight of 80,000 corresponding to 20 m.Eq of a monomeric unit are solubilized in 310 ml of dimethylsulfoxide at 25°. 0.850 g (2 m.Eq) of 21-bromo-4-pregnene-11β,17α-diol-3, 20-dione are added and the resulting solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.4 g of the partial hydrocortisone ester compound in the title are obtained. Quantitative determination of hydrocortisone, after mild alkaline hydrolysis with hydroalcoholic solution of $Na_2$—$CO_3$ and extraction with chloroform, is carried out according to British Pharmacopea, 1980, p. 224.

EXAMPLE 31

Preparation of the (partial) fluorocortisone ester ($C_{21}$) of hyaluronic acid (HA)-20% of esterified carboxylic groups-80% of salified carboxylic groups (Na)

6.2 g of HA tetrabutylammonium salt with a molecular weight of 80,000 corresponding to 10 m.Eq of a monomeric unit are solubilized in 310 ml of dimethylsulfoxide at 25°. 0.89 g (2 m.Eq) of 9-fluoro-21-bromo-4-pregnene-11β,17α-diol-3,20-dione are added and the resulting solution is kept for 12 hours at 30°.

A solution is then added containing 62 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours: at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.6 g of the partial fluorocortisone compound in the title are obtained. Quantitative determination of fluorocortisone, after mild alkaline hydrolysis with hydroalcoholic solution of $Na_2CO_3$ and extraction with chloroform, is carried out according to British Pharmacopea, 1980, p. 196.

EXAMPLE 32

Preparation of the (partial) desoxycorticosterone ester ($C_{21}$) of hyaluronic acid (HA)-20% of esterified carboxylic groups-80% of salified carboxylic groups (Na)

6.21 g of HA tetrabutylammonium salt with a molecular weight of 105,000 corresponding to 10 m.Eq of a monomeric unit are solubilized in 310 ml of dimethylsulfoxide at 25°. 0.661 g (2 m.Eq) of 21-bromo-4-pregnene-3,20-dione are added and the resulting solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 4.5 g of the partial desoxycorticosterone ester compound in the title are obtained. Quantitative determination of desoxycorticosterone, after mild alkaline hydrolysis with hydroalcoholic solution of $Na_2CO_3$ and extraction with chloroform, is carried out according to British Pharmacopea, 1980, p. 137.

EXAMPLE 33

Preparation of the (mixed) ethanol and cortisone ester $(C_{21})$ Of hyaluronic acid (HA)-80% of the carboxylic groups esterified with ethanol-20% of the carboxylic groups esterified with cortisone $(C_{21})$ 6.2 g of HA tetrabutylammonium salt with a molecular weight of 70,000 corresponding to 10 m.Eq of a monomeric unit are solubilized in 310 ml of dimethylsulfoxide at 25°. 1.25 g (8 m.Eq) of ethyl iodide are added and the resulting solution is kept for 12 hours at 30°.

0.85 g (2 m.Eq) of 21-bromo-4-pregnene-17a-ol-3,11,20-trione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is then filtered and washed three times with 100 ml of acetone/water 5:1 and three times with 100 ml of acetone and finally vacuum dried for eight hours at 30°.

4.6 g of the mixed ethanol and cortisone ester compound in the title are obtained. Quantitative determination of cortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 34

Preparation of the (mixed) ethanol and hydrocortisone ester $(C_{21})$ of hyaluronic acid (HA)-80% of carboxylic groups esterified with ethanol-20% of carboxylic groups esterified with hydrocortisone $(C_{21})$ 6.2g of HA tetrabutylammonium salt with a molecular weight of 125,000 corresponding to 10 m.Eq of a monomeric unit are solubilized in 310 ml of dimethylsulfoxide at 25°. 1.25 g (8 m.Eq) of ethyl iodide are added and the solution is kept at 30° for 12 hours.

0.85 g (2 m.Eq) of 21-bromo-4-pregnene-11β, 17α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30° C.

4.6 g of the mixed ethanol and hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030(1961).

EXAMPLE 35

Preparation of the (mixed) ethanol and fluorocortisone ester $(C_{21})$ of hyaluronic acid (HA)-80% of carboxylic groups esterified with ethanol-20% of carboxylic groups 5 esterified with fluorocortisone $C_{21}$ 6.2g of HA tetrabutylammonium salt with a molecular weight of 70,000 corresponding to 10 m.Eq of a monomeric unit are solubilized in 310 ml of dimethylsulfoxide at 25°. 1.25 g (8 m.Eq) of ethyl iodide are added and the solution is kept for 24 hours at 30°.

0.89 g (2 m. Eg.) of 9β-fluoro-21-bromo-4-pregnene-11β, 17α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30° C.

4.6 g of the mixed ethanol and fluorocortisone ester compound featured in the title are obtained. Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030(1961).

EXAMPLE 36

Preparation of the (mixed) ethanol and desoxycorticosterone ester $(C_{21})$ of hyaluronic acid (HA)-80% of carboxylic groups esterified with ethanol-20% of carboxylic groups esterified with desoxycorticosterone $(C_{21})$ 6.2 g of HA tetrabutylammonium salt with a molecular weight of 70,000 corresponding to 10 m.Eq of a monomeric unit are solubilized in 310 ml of dimethylsulfoxide at 25°. 1.25 g (8 m.Eq) of ethyl iodide are added and the resulting solution is kept for 12 hours at 30°.

0.661 g (2 m.Eq ) of 21-bromo-4-pregnene-3,20-dione are added and the solution is kept for 24 hours at 30°. A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.6 g of the mixed ethanol and desoxycorticosterone ester compound in the title are obtained. Quantitative determination of desoxycorticosterone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 37

Preparation of the (partial and mixed) ethanol and desoxycorticosterone ester of hyaluronic acid (HA)-40% of carboxylic groups esterified with desoxycorticosterone ($C_{21}$)-40% of salified carboxylic groups (Na)

6.2 g of HA tetrabutylammonium salt with a molecular weight of 125,000 corresponding to 10 m.Eq of a monomeric unit are 'solubilized in 310 ml of dimethylsulfoxide at 25°. 0.62 g (4 m.Eq) of ethyl iodide are added and the solution is kept for 24 hours at 30°.

0.85 g (2 m.Eq) of 21-bromo-4-pregnene-3,20-dione are added and the solution is kept for 24 hours at 30°. A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and desoxycorticosterone ester compound in the title are obtained. Quantitative determination of desoxycorticosterone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 38

Preparation of the (partial and mixed) ethanol and cortisone ester of hyaluronic acid (HA)-40% of carboxylic groups esterified with ethanol-20% of carboxylic groups esterified with cortisone ($C_{21}$)-40% of salified carboxylic groups (Na)

6.2 g of HA tetrabutylammonium salt with a molecular weight of 125,000 corresponding to 10 m.Eq of a monomeric unit are solubilized in 310 ml of dimethylsulfoxide at 25°. 0.62 g (4 m.Eq) of ethyl iodide are added and the solution is kept for 24 hours at 30°.

0.85 g (2 m.Eq) of 21-bromo-4-pregnene-17α-ol -3,11,20-trione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and cortisone compound in the title are obtained. Quantitative determination of cortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 39

Preparation of the (partial and mixed) ethanol and hydrocortisone ester ($C_{21}$) of hyaluronic acid (HA)-40% of carboxylic groups esterified with ethanol-20% of carboxylic groups esterified with hydrocortisone ($C_{21}$) -40% of salified carboxylic groups (Na)

6.2 g of HA tetrabutylammonium salt with a molecular weight of 70,000 corresponding to 10 m.Eq of a monomeric unit are solubilized in 310 ml of dimethylsulfoxide at 25°. 0.62 g (4 m.Eq) of ethyl iodide are added and the solution is kept for 24 hours at 30°.

0.85 g (2 m.Eq) of 21-bromo-4-pregnene-11β,17α-diol-3,20-dione are added and the solution is kept for 24 hours at 30°.

A solution is then added containing 200 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

4.5 g of the partial and mixed ethanol and hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 40

Preparation of the (partial and mixed) ethanol and fluorocortisone esters ($C_{21}$) of hyaluronic acid (HA)-40% of carboxylic groups esterified with ethanol-20% of carboxylic groups esterified with fluorocortisone ($C_{21}$) -40% of salified carboxylic groups (Na)

6.2 g of HA tetrabutylammonium salt with a molecular weight of 65,000 corresponding to 20 m.Eq of a monomeric unit are solubilized in 310 ml of dimethylsulfoxide at 25°. 0.62 g (4 m.Eq) of ethyl iodide are added and the solution is kept for 24 hours at 30°.

0.89 g (2 m.Eq) of 9β-fluoro-21-bromo-4-pregnene -11β, 17α-diol-3,20-dione are added and the solution is kept for 24 hours at 30°.

15 A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml ethyl acetone and finally vacuum dried for eight hours at 30°.

4.6 g of the partial and mixed ethanol and fluorocortisone ester in the title are obtained. Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas, Anal. Chem. 33, 1028–1030 (1961).

EXAMPLE 41

Preparation of the streptomycin salt of hyaluronic acid (HA) partially esterified with ethanol-75% of carboxylic groups esterified with ethanol-25% of carboxylic groups salified with streptomycin 243 mg of streptomycin sulphate (1 m.Eq) are solubilized in 20 ml of water. The solution is eluted in a thermostatic column at 5° containing 2 ml of quaternary ammonium resin (Dowex 1×8) in the OH form.

The sulphate-free eluate is gathered in a thermostatic container at a temperature of 5°.

1.6 g of a 75% ethyl ester of HA and 25% sodium salt (corresponding to 1 m.Eq of a monomeric unit relative to the non-esterified carboxyl) are solubilized in 400 ml of water. The solution is eluted in a thermostatic column at 20° and containing 2 ml of sulphonic resin (Dowex 50×8) in the H⁺ form.

The sodium-free eluate is gathered under agitation in the solution of streptomycin base. The resulting solution is instantly frozen and freeze-dried. Yield: 1.7 g.

Microbiological determination on *B. subtilis* ATCC 6633 in comparison with streptomycin standard shows a content of 10.9% by weight of streptomycin base, corresponding to the theoretically calculated content.

EXAMPLE 42

Preparation of the erythromycin salt of hyaluronic acid (HA) partially esterified with ethanol-75% of carboxylic groups esterified with ethanol-25% of carboxylic groups salified with erythromycin 1.6 g of a 75% ethyl ester of HA and sodium salt at 25% (corresponding to m.Eq of a monomeric unit relative to the non-esterified carboxyl are solubilized in 400 ml of water. The solution is eluted in a thermostatic column at 20° containing 2 ml of sulfonic resin (Dowex 50×8) in the H⁺ form.

To the sodium-free eluate are added 734 mg of erythromycin base (1 m.Eq). The resulting solution is instantly frozen and freeze-dried. Yield: 2.1 g.

Microbiological determination on *S. aureus* ATCC 6538 in comparison to standard erythromycin shows a content of 31.7% by weight of erythromycin base, corresponding to the theoretically calculated weight.

EXAMPLE 43

Preparation of the neomycin salt of hyaluronic acid partially esterified with ethanol-75% of carboxylic groups esterified with ethanol-25% of carboxylic groups salified with neomycin 152 mg of neomycin sulfate (1 m.Eq) are solubilized in 20 ml of water. The solution is eluted in a thermostatic column at 5° containing 2 ml of quaternary ammonium resin (Dowex 1×8) in the OH⁻ form.

The sulphate-free eluate is gathered in a thermostatic container at a temperature of 5°.

1.6 g of a 75% ethyl ester of HA and sodium salt at 25% (corresponding to 1 m. Eq. of monomeric unit relative to the non-esterified carboxyl) are solubilized in 400 ml of water. The solution is eluted in a thermostatic column at 20° and containing 2 ml of sulfonic resin (Dowex 50×8) in the H⁺ form.

The sodium-free eluate is gathered under agitation in the solution of neomycin base. The resulting solution is instantly frozen and freeze-dried. Yield: 1.65 g.

Microbiological determination carried out on *S. aureus* ATCC 6538 in comparison to standard neomycin shows a content of 6.1% by weight of neomycin base, corresponding to the theoretically calculated value.

EXAMPLE 44

Preparation of the gentamicin salt of hyaluronic acid (HA) partially esterified with ethanol-75% of carboxylic groups esterified with ethanol-25% of carboxylic groups salified with gentamicin 145 mg of gentamicin sulfate are solubilized in 10 ml of water. The solution is eluted in a thermostatic column at 5° containing 2 ml of quaternary ammonium resin (Dowex 1×8) in the OH⁻ form.

The sulphate-free eluate is gathered in a thermostatic container at a temperature of 5°.

1.6 g of a 75% ethyl ester of HA and sodium salt at 25% (corresponding to 1 m.Eq of a monomeric unit relative to the non-esterified carboxyl) are solubilized in 400 ml of water. The solution is eluted in a thermostatic column at 20° and containing 2 ml of sulfonic resin (Dowex 50×8) in the H⁺ form.

The sodium-free eluate is gathered under agitation in the solution of gentamicin base. The resulting solution is instantly frozen and freeze-dried. Yield: 1.7 g.

Microbiological determination carried out on *S. epidermidus* ATCC 12228 in comparison to standard gentamicin shows a content of 6.50% by weight of gentamicin base, corresponding to the theoretically calculated value.

EXAMPLE 45

Preparation of the amikacin salt of hyaluronic acid (HA) partially esterified with ethanol-75% of carboxylic groups esterified with ethanol-25% of carboxylic groups salified with amikacin 147 mg of amikacin (1 m.Eq) are solubilized in 20 ml of water.

1.6 g of a 75% ethyl ester of HY and sodium salt at 25% (corresponding to 1 m.Eq of a monomeric unit relative to the non-esterified carboxyl) are solubilized in 400 ml of water. The solution is eluted in a thermostatic column at 20° and containing 2 ml of sulfonic resin (Dowex 50×8) in the H⁺ form.

The sodium-free eluate is gathered under agitation in the solution of amikacin base. The resulting solution is instantly frozen and freeze dried. Yield: 1.70 g.

Microbiological determination carried out on *S. aureus* ATCC 29737 in comparison to standard amikacin shows a content of 8.5% by weight of amikacin base, corresponding to the theoretically calculated value.

EXAMPLE 46

Preparation of the kanamycin salt of hyaluronic acid (HA) partially esterified with ethanol-75% of carboxylic groups esterified with ethanol-25% of carboxylic groups salified with kanamycin 146 mg of kanamycin sulfate (1 m.Eq) are solubilized in 20 ml of water. The solution is eluted in a thermostatic column at 5° containing 2 ml of quaternary ammonium resin (Dowex 1×8) in the OH⁻ form.

The sulphate-free eluate is gathered in a thermostatic container at a temperature of 5°.

1.6 g of a 75% ethyl ester of HA and sodium salt at 25% (corresponding to 1 m.Eq of a monomeric unit relative to the non-esterified carboxyl) are solubilized in 400 ml of water. The solution is eluted in a thermostatic column at 20° and containing 2 ml of sulfonic resin (Dowex 50×8) in the H⁺ form.

The sodium-free eluate is gathered under agitation in the solution of kanamycin base. The resulting solution is instantly frozen and freeze-dried. Yield: 1.5 g.

Microbiological determination carried out on *B. subtilis* ATCC 6633 in comparison to standard kanamycin shows a content of 7% by weight of kanamycin base, corresponding to the theoretically calculated value.

EXAMPLE 47

Preparation of the pilocarpine salt of hyaluronic acid (HA) Partially esterified with ethanol-75% of carboxylic groups esterified with ethanol-25% of carboxylic groups salified with pilocarpine 245 mg of pilocarpine hydrochloride (1 m.Eq) are solubilized in 20 ml of water. The solution is eluted in a thermostatic column at 5° containing 2 ml of quaternary ammonium resin (Dowex 1×8) in OH⁻ form.

The chloride-free eluate is gathered in a thermostatic container at 5°.

1.6 g of a 75% ethyl ester of HA and sodium salt at 25% (corresponding to 1 m.Eq of a monomeric unit relative to the non-esterified carboxyl) are solubilized in 400 ml of water. The solution is eluted in a thermostatic column at 20° and containing 2 ml of sulfonic resin (Dowex 50×8) in the H⁺ form.

The sodium-free eluate is gathered under agitation in the solution of pilocarpine base. The resulting solution is instantly frozen and freeze-dried. Yield: 1.89 g.

EXAMPLE 48

Preparation of the pilocarpine salt of hyaluronic acid (HA) partially esterified with n-propanol-85% of carboxylic groups esterified with n-propanol-15% of carboxylic groups salified with pilocarpine 245 mg of pilocarpine hydrochloride (1 m.Eq) are solubilized in 10 ml of water. The solution is eluted in a thermostatic column at 5° containing 2 ml of quaternary ammonium resin (Dowex 1×8) in the OH⁻ form.

The chloride-free eluate is gathered in a thermostatic container at 5°.

4.1 g of the 85% propyl ester of HA and tetrabutylammonium salt at 15% (corresponding to 1 m.Eq of a monomeric unit relative to the nonesterified carboxyl) are solubilized in 100 ml of dimethylsulfoxide. The solution is eluted in a thermostatic column at 20° containing 2 ml of damp sulfonic resin (Dowex 50×8) in the H⁺ form.

The eluate is gathered under agitation in the solution of pilocarpine base. The resulting solution is precipitated with ethyl acetate (600 ml).

The precipitate is filtered and washed four times with 200 ml of ethyl acetate and finally vacuum dried for 24 hours at 30°. 3.5 g of the compound featured in the title are obtained.

The following examples illustrate the preparation of films by evaporation of solvent from mixtures of hyaluronic acid ester with benzyl alcohol (25% esterification, HYAFF11 p25) dissolved in DMSO and polymers soluble in DMSO.

The solution of HYAFF11 p25 in DMSO is prepared as follows: 100 mg of HYAFF11 p25 are dissolved in distilled water: DMSO, 1:1, while being shaken at room temperature for 30 minutes. The water is then substituted with DMSO by adding the second solvent to the solution and heating it to 90° C. until all the water has evaporated. Lastly, the solution is brought to a final volume of 10 ml with DMSO. A 1% solution of HYAFF11 p25 is thus obtained, and will be referred to as solution A in examples 49–55.

EXAMPLE 49

Preparation of a film containing HYAFF11p25 and polyvinyl alcohol (PVA)

100 mg of PVA are dissolved in DMSO while being shaken at a temperature of 100° C. for one hour and are then brought to a final volume of 10 ml. A 1% solution of PVA is thus obtained, which will be referred to as solution B.

Solution A is slowly added to solution B while being continuously shaken at a temperature of 100° C. The resulting solution is shaken for one hour to allow complete amalgamation of the two components.

The resulting solution, containing the mixture of HYAFF11p25/PVA in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 50

Preparation of a film containing HYAFF11p25 and Clarene L6, Solvay (Cl L6), ethylene-vinyl alcohol copolymer with a low ethylene content (29 mole %)

100 mg of Cl L6 are dissolved in DMSO while being shaken at a temperature of 70° C. for one hour and are then brought to a final volume of 10 ml. A 1% solution of Cl L6 is thus obtained, which will be referred to as solution C.

Solution A is slowly added to solution C while being continuously shaken at a temperature of 70° C. The resulting solution is shaken for one hour to allow complete amalgamation of the two components.

The resulting solution, containing the mixture of HYAFF11p25/Cl L6 in a weight ratio of 20/80, is poured into a polystyrene Petri dish and placed into a ventilation oven set at a temperature of 75° C. Once the solvent has completely evaporated, a transparent and homogeneous film is obtained.

EXAMPLE 51

Preparation of a film containing HYAFF11p25 and Clarene P10, Solvay (Cl P10), ethylene-vinyl alcohol copolymer with a medium ethylene content (36 mole %)

100 mg of Cl P10 are dissolved in DMSO while being shaken at a temperature of 70° C. for one hour and are then brought to a final volume of 10 ml. A 1% solution of Cl P10 is thus obtained, which will be referred to as solution D.

Solution A is slowly added to solution D while being shaken continuously at a temperature of 80° C. The resulting solution is shaken for one hour to allow complete amalgamation of the two components.

The resulting solution, containing the mixture of HYAFF11p25/Cl P10 in a weight ratio of 20/80, is poured into a polystyrene Petri dish and placed into a ventilation oven set at a temperature of 75° C. Once the solvent has completely evaporated, a transparent and homogeneous film is obtained.

EXAMPLE 52

Preparation of a film containing HYAFF11p25 and Clarene R20, Solvay (Cl R20), ethylene-vinyl alcohol copolymer with a high ethylene content (40 mole %)

100 mg of Cl R20 are dissolved in DMSO while being shaken at a temperature of 70° C. for one hour and are then brought to a final volume of 10 ml. A 1% solution of Cl R20 is thus obtained, which will be referred to as solution E.

Solution A is slowly added to solution E while being continuously shaken at a temperature of 70° C. The resulting solution is shaken for one hour to allow complete amalgamation of the two components.

The resulting solution containing the mixture of HYAFF11 p25/Cl R20 in a weight ratio of 20/80 is poured

EXAMPLE 53

Preparation of a film containing HYAFF11p25 and polyurethane (PU), Cardiomat 610, Contron 0.670 ml of a 15% solution of PU in tetrahydrofuran:dioxane, 1:1, are dissolved in 8 ml of DMSO, while being shaken at a temperature of 70° C. for one hour. When the starting solvents have evaporated, the solution is brought to a final volume of 10 ml with DMSO. A 1% solution of PU is thus obtained, which will be referred to as solution F.

Solution A is slowly added to solution F while being continuously shaken at a temperature of 70° C. The resulting solution is shaken for one hour to allow complete amalgamation of the two components.

The resulting solution, containing the mixture HYAFF11 p25/PU in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 54

Preparation of a film containing HYAFF11 p25 and polylactic acid (PLA)

100 mg of PLA are dissolved in DMSO while being shaken at a temperature of 85° C. for one hour and are then brought to a final volume of 10 ml. A 1% solution of PLA is thus obtained, which will be referred to as solution G.

Solution A is slowly added to solution G while being continuously shaken at a temperature of 85° C. The resulting solution is shaken for one hour to allow complete amalgamation of the two components.

The resulting solution, containing the mixture of HYAFF11 p25/PLA in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 55

Preparation of a film of HYAFF11 p25 and polyphosphazene, for example poly (methoxyethoxy) phosphazene (PF3)

100 mg of PF3 are dissolved in DMSO while being shaken at a temperature of 100° C. for one hour and are then brought to a final volume of 10 ml. A 1% solution of PF3 is thus obtained, which will be referred to as solution H.

Solution A is slowly added to solution H while being constantly shaken at a temperature of 100° C. The resulting solution is shaken for one hour to allow complete amalgamation of the two components.

The resulting solution containing the mixture of HYAFF11 p25/PF3 in a weight ratio of 20/80 is poured into a polystyrene Petri dish and placed in a ventilation oven set at a temperature of 75° C. Once the solvent has completely evaporated, a transparent and homogeneous film is obtained.

The following example illustrates the preparation of a film by the evaporation of solvent from mixtures of hyaluronic acid esters with benzyl alcohol (50% esterification, HYAFF11 p50) dissolved in DMSO and polymers soluble in DMSO.

The solution of HYAFF11 p50 in DMSO is prepared as follows: 100 mg of HYAFF11 p50 are dissolved in distilled water: DMSO, 1:1, while being shaken at room temperature for 30 minutes. The water is then substituted with DMSO by adding the latter to the solution and heating to 90° C. to evaporate the water. Lastly, the solution is brought to a final volume of 10 ml with DMSO. A 1% solution of HYAFF11 p50 in DMSO is thus obtained, and will be referred to as solution A in Example 56.

EXAMPLE 56

Preparation of a film containing HYAFF11 p50 and polyphosphazene, for example poly (methoxyethoxy) phosphazene (PF3)

100 mg of PF3 are dissolved in DMSO while being shaken at a temperature of 100° C. for one hour and are then brought to a final volume of 10 ml. A 1% solution of PF3 is thus obtained, and this will be referred to as solution B.

Solution A is slowly added to solution B while being shaken at a temperature of 100° C. The solution is shaken for one hour to allow complete amalgamation of the two components.

The resulting solution containing the mixture of HYAFF11 p50/PF3 in a weight ratio of 20/80 is poured into a polystyrene Petri dish and placed in a ventilation oven set at a temperature of 75° C. Once the solvent has completely evaporated, a transparent and homogeneous film is obtained.

The following examples illustrate the preparation of films by the evaporation of solvent from mixtures of hyaluronic acid esters with benzyl alcohol (75% esterification, HYAFF11 p75) dissolved in DMSO and polymers soluble in DMSO.

100 mg of HYAFF11 p75 are dissolved in DMSO while being shaken at room temperature for 30 minutes. DMSO is then added to a final volume of 10 ml. A 1% solution of HYAFF11 p75 is thus obtained, which will be referred to as solution A in examples 57–62.

EXAMPLE 57

Preparation of a film containing HYAFF11 p75 and polyvinyl alcohol (PVA)

100 mg of PVA are dissolved in DMSO while being shaken at a temperature of 100° C. for one hour and are then brought to a final volume of 10 ml. A 1% solution of PVA is thus obtained, which will be referred to as solution B.

Solution A is slowly added to solution B while being constantly shaken at a temperature of 100° C. The resulting solution is shaken for one hour to allow complete amalgamation of the two components.

The resulting solution, containing the mixture of HYAFF11 p75/PVA in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 58

Preparation of a film containing HYAFF11 p75 and Clarene L6, Solvay (Cl L6), ethylene-vinyl copolymer with a low ethylene content (29 mole %)

100 mg of Cl L6 are dissolved in DMSO while being shaken at a temperature of 70° C. for one hour and are then brought to a final volume of 10 ml. A 1% solution of Cl L6 is thus obtained, which will be referred to as solution C.

Solution A is slowly added to solution C while being constantly shaken at a temperature of 70° C. The resulting solution is shaken for one hour to allow complete amalgamation of the two components.

The resulting solution, containing the mixture of HYAFF11 p75/C1 L6 in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 59

Preparation of a film containing HYAFF11 p75 and Clarene P10, Solvay (C1 P10), ethyl-vinyl alcohol copolymer with a medium ethylene content (36 mole %)

100 mg of C1 P10 are dissolved in DMSO while being shaken at a temperature of 70° C. for one hour and are then brought to a final volume of 10 ml. A 1% solution of C1 P10 is thus obtained which will be referred to as solution D.

Solution A is slowly added to solution D while being constantly shaken at a temperature of 70° C. The resulting solution is shaken for one hour to allow complete amalgamation of the two components.

The resulting solution, which contains HYAFF11 p75/C1 P10 in a weight ratio of 20/80, is slowly poured into a polystyrene Petri dish and placed in a ventilation oven set at a temperature of 75° C. Once the solvent has completely evaporated, a transparent and homogeneous film is obtained.

EXAMPLE 60

Preparation of a film containing HYAFF11 p75 and Clarene R20, Solvay (C1 R20), ethylene-vinyl alcohol copolymer with a high ethylene content (40 mole %)

100 mg of C1 R20 are dissolved in DMSO while being shaken at a temperature of 70° C. for one hour and are then brought to a final volume of 10 ml. A 1% solution of C1 R20 is thus obtained, which will be referred to as solution E.

Solution A is slowly added to solution E while being constantly shaken at a temperature of 70° C. The resulting solution is shaken for one hour to allow complete amalgamation of the two components.

The resulting solution, containing the mixture of HYAFF11 p75/C1 R20 in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 61

Preparation of a film containing HYAFF11 p75 and polyurethane (PU), Cardiomat 610, Contron 0.670 ml of a 15% PU solution in tetrahydrofuran:dioxane, 1:1, are dissolved in 8 ml of DMSO while being shaken at a temperature of 70° C. for one hour. When the starting solvents have evaporated, the solution is brought to a final volume of 10 ml with DMSO. A 1% solution of PU is thus obtained, which is referred to as solution F.

Solution A is slowly added to solution F while being constantly shaken at a temperature of 70° C. The resulting solution is shaken for one hour to allow complete amalgamation of the two components.

The resulting solution, containing the mixture of HYAFF11 p75/PU in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 62

Preparation of a film containing HYAFF11 p75 and polylactic acid (PLA)

100 mg of PLA are dissolved in DMSO while being constantly shaken at a temperature of 85° C. for one hour and are then brought to a final volume of 10 ml. A 1% solution of PLA is thus obtained, which will be referred to as solution G.

Solution A is slowly added to solution G while being constantly shaken at a temperature of 85° C. The resulting solution is shaken for one hour to allow complete amalgamation of the two components.

The resulting solution, containing the mixture of HYAFF11 p75/PLA in a weight ratio of 20/80, is poured into a polystyrene Petri dish and placed in a ventilation oven set at a temperature of 75° C. Once the solvent has completely evaporated, a transparent and homogeneous film is obtained.

The following examples describe the preparation of films by the evaporation of solvent from mixtures of hyaluronic acid esters with benzyl alcohol (100% esterification, HYAFF11 dissolved in DMSO and polymers soluble in DMSO. 100 mg of HYAFF11 are dissolved in DMSO while being shaken at room temperature for 30 minutes. DMSO is then added until a final volume of 10 ml is reached. A 15% solution of HYAFF11 in DMSO is thus obtained, which will be referred to as solution A in examples 63–69.

EXAMPLE 63

Preparation of a film of HYAFF11 and polyvinyl alcohol (PVA) 100 mg of PVA are dissolved in DMSO while being shaken at a temperature of 100° C. for one hour and are then brought to a final volume of 10 ml. A 1% solution of PVA is thus obtained, which will be referred to as solution B.

Solution A is slowly added to solution B while being constantly shaken at a temperature of 100° C. The resulting solution is shaken for one hour to allow complete amalgamation of the two components.

The resulting solution, containing the mixture of HYAFF11 /PVA in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 64

Preparation of a film containing HYAFF11 and Clarene L6, Solvay (C1 L6), ethylene-vinyl alcohol copolymer with a low ethylene content (29 mole %)

100 mg of C1 L6 are dissolved in DMSO while being shaken at a temperature of 70° C. for one hour and are then brought no a final volume of 10 ml. A 1% solution of C1 L6 is thus obtained, which will be referred to as solution C.

Solution A is slowly added to solution C while being constantly shaken at a temperature of 70° C. The resulting solution is shaken for one hour to allow complete amalgamation of the two components.

The resulting solution, containing the mixture of HYAFF11/C1 L6 in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 65

Preparation of a film containing HYAFF11 and Clarene P10, Solvay (C1 P10), ethylene-vinyl alcohol copolymer with a medium ethylene content (36 mole %)

100 mg of C1 P10 are dissolved in DMSO while being shaken at a temperature of 70° C. for one hour and are then brought to a final volume of 10 ml. A 1% solution of C1 P10 is thus obtained, which will be referred to as solution D.

Solution A is slowly added to solution D while being constantly shaken at a temperature of 70° C. The resulting solution is shaken for one hour to allow complete amalgamation of the two components.

The resulting solution, containing the mixture of HYAFF11 /C1 P10 in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 66

Preparation of a film containing HYAFF11 and Clarene P20, Solvay (C1 R20), ethylene-vinyl alcohol copolymer with a high ethylene content (40 mole %)

100 mg of C1 R20 are dissolved in DMSO while being shaken at a temperature of 70° C. for one hour and are then brought to a final volume of 10 ml. A 1% solution of C1 R20 is thus obtained, which will be referred to as solution E.

Solution A is slowly added to solution E while being constantly shaken at a temperature of 70° C. The resulting solution is shaken for one hour to allow complete amalgamation of the two components.

The resulting solution, containing the mixture of HYAFF11 /C1 R20 in a weight ratio of 20/80, is poured into a polystyrene Petri dish and placed into a ventilation oven set at a temperature of 75° C. Once the solvent has evaporated, a transparent and homogeneous film is obtained.

EXAMPLE 67

Preparation of a film containing HYAFF11 and polyurethane (PU), Cardiomat 610, Controt 0.670 ml of a 15% solution of PU in tetrahydrofuran:dioxane, 1:1, are dissolved in DMSO while being shaken at a temperature of 70° C. for one hour. When the starting solvents have evaporated, the solution is brought to a final volume of 10 ml with DMSO. A 1% solution of PU is thus obtained, which will be referred to as solution F.

Solution A is slowly added to solution F while being shaken at a temperature of 70° C. The resulting solution is shaken for one hour to allow complete amalgamation of the two components.

The resulting solution, containing the mixture of HYAFF11 /PU in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 68

Preparation of a film containing HYAFF11 and polylactic acid (PLA)

100 mg of PLA are dissolved in DMSO while being shaken at a temperature of 85° C. for one hour and are then brought to a final volume of 10 ml. A 1% solution of PLA is thus obtained, which will be referred to as solution G.

Solution A is slowly added to solution G while being constantly shaken at a temperature of 85° C. The resulting solution is shaken for one hour to allow complete amalgamation of the two components.

The resulting solution, containing the mixture of HYAFF11/PLA in a weight ratio of 20/80, is poured into a polystyrene Petri dish and placed in a ventilation oven set at a temperature of 75° C. Once the solvent has completely evaporated, a transparent and homogeneous film is obtained.

EXAMPLE 69

Preparation of a film containing HYAFF11 and polyphosphazene, for example poly-phenoxy phosphazene 100 mg of PF4 are dissolved in DMSO while being shaken at a temperature of 25° C. for one hour and brought to a final volume of 10 ml. A 1% solution of PF4 is thus obtained, which will be referred to as solution H.

Solution A is slowly added to solution H while shaking at a temperature of 25° C. The resulting solution is shaken for one hour to allow complete amalgamation of the two components.

The resulting solution, containing the mixture of HYAFF11/PF4 in a weight ratio of 20/80, is poured into a polystyrene Petri dish and placed in a ventilation oven set at a temperature of 75° C. Once the solvent has completely evaporated, a transparent and homogeneous film is obtained.

Crosslinking of preformed Polymers

In order to attain the objects of the present invention, all the polymer blends produced in the foregoing examples can be transformed into additional IPN or semi-IPN by the following methods.

EXAMPLE 70

Crosslinking of polymers using compounds capable of generating radicals

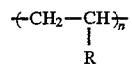

in which R can be H, halogen, $SOCl_2$, COCl, $SO_3H$, COOH, or COOR' can be crosslinked with many peroxides (Solovey et al., Bell System Tech. J., 40:1400, 1961). The working temperatures are very high, leading to polymer degradation.

Aliphatic polyethers, such as polyethyleneoxide and polypropyleneoxide may be crosslinked through peroxides (Y. Okada, J. Appl. Polym. Sci, 7:695, 703, and 1153, 1963).

Polyamides, polysulphones, and polyesters can be crosslinked using peroxides.

Besides peroxides, ethyltrichloroacetate, $C_6H_{11}$—$CCl_3$, R—S—S—R, etc., can be used to generate radicals.

With preformed polymers having C—C double bonds, "two reagent systems" can be used: one reagent generates radicals, while the second works as an intermolecular bridge between the double bonds. An example thereof is peroxide-dimaleimide.

Crosslinking of polymers having various functional groups

Carboxylic functional groups: polyacrylic acid, polymethacrylic acid and their copolymers with acrylate, methacrylate, styrene, and other vinylic monomers, the copolymers of hydrolyzed maleic anhydride and sorbic acid, may be crosslinked with diamine, triamine, di- and polyisocyanate, di-, tri-, and polyols, N-methylol derivatives of formaldehyde, oxiranic compounds, and carbodiimide. At high temperatures, the crosslink can occur by the formation of intermolecular anidridic groups.

OH functional groups: polyvinylic alcohol and its copolymers with ethylene, acrylate, methacrylate, betahydroxyethyl-acrylate, copolymers with styrene-beta-hydroxyethylacrylate may be crosslinked through formaldehyde, N-methylol derivatives of formaldehyde, dihalogenides of carboxylic acids, glyoxal glutaraldehyde, and other dialdehydes.

Mixtures of linear polymers having functional groups such as polyvinylic alcohol or its copolymers with polyacrylic or polymethacrylic acid may be crosslinked through intermolecular esterification (Y. Tatara, J. Polym. Sci. Symp. 54:283, 1976). These mixtures may also be crosslinked through the above-mentioned reagents for —COOH and —OH groups.

For cellulose, the following compounds have been used as crosslinking reagents: urea-formaldehyde, dimethylol-urea, bis-dimethylol derivatives of cyclic ethylene-urea, and similar compounds such as methylol-tetramethylene-urea, N-methylol derivatives of idanthoine, of imizadolidone, of propylene-urea, and triazones. Other useful compounds are glyoxal, glutaraldehyde, alpha-hydroxyadipaldehyde, and other dialdehydes, diepoxides, such as cyclohexenedioxide, and others having the general structure:

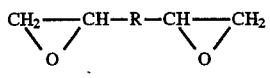

which can be derivatized with ethyleneamine, sulphones, and alpha-chloroether.

Amino-ureic-urethanic functional groups: polyamides, polyurea, and polyurethanes can be crosslinked using di- and polyisocyanates.

Besides the foregoing methods of obtaining IPN and semi-IPN by crosslinking both of the components of the blend, semi-IPN can also be obtained by the polymerization of a monomer in the presence of a crosslinking agent and in the presence of the natural acidic polysaccharide or a semi-synthetic ester-type derivative thereof.

As an example, it has been possible to obtain a semi-IPN by polymerizing metha-methacrylate, in which the polysaccharide has been dissolved, in the presence of tetraethylene glycol dimethacrylate (TEGDM) as the crosslinking agent and benzoin as initiator using a UV photopolymerization process in bulk.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A biomaterial, comprising a non-chemically crosslinked interpenetrating polymer network, IPN, having a first component and a second component wherein said first component is a member selected from the group consisting of a hyaluronic acid ester and a salt of hyaluronic acid with an organic base, and said second component is a synthetic chemical polymer.

2. The biomaterial of claim 1, wherein said first component is a hyaluronic acid ester and wherein said hyaluronic acid ester is a 100% hyaluronic acid ester or a partial hyaluronic acid ester.

3. The biomaterial of claim 2, wherein said hyaluronic acid ester is 100% hyaluronic acid ester and wherein said 100% hyaluronic acid ester is a member selected from the group consisting of a 100% benzyl ester of hyaluronic acid and a 100% ethyl ester of hyaluronic acid, and said partial hyaluronic acid ester is a member selected from the group consisting of a 10% partial benzyl ester of hyaluronic acid, a 25% partial benzyl ester of hyaluronic acid, a 50% partial benzyl ester of hyaluronic acid, and a 75% partial benzyl ester of hyaluronic acid.

4. The biomaterial of claim 1, wherein said first component is a hyaluronic acid ester and wherein said hyaluronic acid ester is a partial or total hyaluronic acid ester containing an alcohol having a chain length of 14 carbon atoms or less.

5. The biomaterial of claim 1, wherein said first component is a hyaluronic acid ester and wherein said hyaluronic acid ester is an ester of hyaluronic acid with an aliphatic, araliphatic, cycloaliphatic, or heterocyclic alcohol.

6. The biomaterial of claim 1, wherein said organic base is a pharmacologically active molecule.

7. The biomaterial of claim 6, wherein said pharmacologically active molecule is a member selected from the group consisting of an antiinfective agent, an antibiotic agent, an antimicrobial agent, an antiinflammatory agent, a cytostatic agent, a cytotoxic agent, an antiviral agent, an anaesthetic agent, an antiseptic agent, and a disinfecting agent.

8. The biomaterial of claim 1, wherein said hyaluronic acid ester is an ester with a pharmacologically active molecule.

9. The biomaterial of claim 8, wherein said pharmacologically active molecule is a member selected from the group consisting of an antiinfective agent, an antibiotic agent, an antimicrobial agent, an antiinflammatory agent, a cytostatic agent, a cytotoxic agent, an antiviral agent, an anaesthetic agent, an antiseptic agent, and a disinfecting agent.

10. The biomaterial of any one of claims 1–9, wherein the polymers comprising said IPN are soluble in dimethylsulfoxide.

11. The biomaterial of claim 1, wherein said synthetic chemical polymer is grafted onto said hyaluronic acid ester or salt of hyaluronic acid with an organic base.

12. The biomaterial of claim 11, wherein the grafting is achieved via functional groups on said hyaluronic acid ester or salt of hyaluronic acid with an organic base and said synthetic chemical polymer.

13. The biomaterial of claim 12, wherein said IPN is formed prior to grafting.

14. The biomaterial of claim 1, wherein said biomaterial is in a form selected from the group consisting of a film, a membrane, a sponge, a hydrogel, a guide channel, a thread, a gauze, and a non-woven tissue.

15. The biomaterial of claim 1, further comprising a therapeutic agent selected from the group consisting of an antiinfective agent, an antibiotic agent, an antimicrobial agent, an antiinflammatory agent, a cytostatic agent, a cytotoxic agent, an antiviral agent, an anaesthetic agent, an antiseptic agent, and a disinfecting agent.

16. The biomaterial of claim 1, wherein said synthetic chemical polymer is a member selected from the group consisting of polyacrylic acid, polyvinylpyrrolidone, potyacrylamide, polyethylene oxide, vinyl alcohol-vinyl acetate copolymer, polyvinyl alcohol, poly-(trifluoroethoxy) phosphazene, poly-(di (p-sodiosulfoxyphenoxy) phosphazene), poly(methoxyethoxy) phosphazene, poly (phenoxy) phosphazene, ethylene-vinyl alcohol copolymer polyurethane, and polylactic acid.

17. The biomaterial of claim 2, wherein in said partial hyaluronic acid ester, the free carboxylic acid groups are salified with a metal or an organic base.

18. The biomaterial of claim 17, wherein said metal is an alkali metal or alkaline earth metal.

19. The biomaterial of claim 17, wherein said organic base is ammonia or a nitrogenous organic base.

* * * * *